(12) United States Patent
Yoon et al.

(10) Patent No.: US 11,679,138 B2
(45) Date of Patent: Jun. 20, 2023

(54) VIBRIO PARAHAEMOLYTICUS BACTERIOPHAGE VIB-PAP-7 AND USE OF SAME FOR INHIBITING VIBRIO PARAHAEMOLYTICUS BACTERIA PROLIFERATION

(71) Applicant: Intron Biotechnology, Inc., Gyeonggi-do (KR)

(72) Inventors: Seong Jun Yoon, Seoul (KR); Soo Youn Jun, Seoul (KR); An Sung Kwon, Gyeonggi-do (KR); Hyun Min Song, Seoul (KR); Eun Ji Lee, Gyeonggi-do (KR); Sang Hyeon Kang, Seoul (KR)

(73) Assignee: Intron Biotechnology, Inc., Gyeonggi-do (KR)

( * ) Notice: Subject to any disclaimer, the term of this patent is extended or adjusted under 35 U.S.C. 154(b) by 318 days.

(21) Appl. No.: 16/611,877

(22) PCT Filed: Mar. 8, 2018

(86) PCT No.: PCT/KR2018/002734
§ 371 (c)(1),
(2) Date: Nov. 8, 2019

(87) PCT Pub. No.: WO2018/208001
PCT Pub. Date: Nov. 15, 2018

(65) Prior Publication Data
US 2021/0138005 A1    May 13, 2021

(30) Foreign Application Priority Data

May 10, 2017 (KR) .................. 10-2017-0058068

(51) Int. Cl.
*A61K 35/76* (2015.01)
*A61P 31/04* (2006.01)
(Continued)

(52) U.S. Cl.
CPC ............ *A61K 35/76* (2013.01); *A23K 20/195* (2016.05); *A23K 50/80* (2016.05); *A61P 31/04* (2018.01);
(Continued)

(58) Field of Classification Search
CPC .................................. A61K 35/76; C12N 7/00
See application file for complete search history.

(56) References Cited

U.S. PATENT DOCUMENTS 9,504,721 B2    11/2016  Sung et al.
9,956,256 B2    5/2018   Shin et al.
(Continued)

FOREIGN PATENT DOCUMENTS

KR    20140000541 A    1/2014
KR    101536901 B1     7/2015
(Continued)

OTHER PUBLICATIONS

World Health Organization, "Risk assessment of Vibrio parahaemolyticus in seafood: interpretative summary and technical report", World Health Organization, 16, pp. 32-33 (Year: 2012).*

(Continued)

*Primary Examiner* — Michelle F. Paguio Prising
*Assistant Examiner* — Grant C Currens
(74) *Attorney, Agent, or Firm* — Ballard Spahr LLP

(57) ABSTRACT

The present invention relates to a Myoviridae bacteriophage Vib-PAP-7 (Accession number: KCTC 13247BP) isolated from nature, which has the ability to kill *Vibrio parahaemolyticus* and has the genome represented by SEQ ID NO: 1, and a method for preventing or treating a disease caused by *Vibrio parahaemolyticus* using a composition containing the Myoviridae bacteriophage Vib-PAP-7 as an active ingredient.

1 Claim, 1 Drawing Sheet
Specification includes a Sequence Listing.

(51) Int. Cl.
    *C12N 7/00*         (2006.01)
    *A23K 20/195*       (2016.01)
    *A23K 50/80*        (2016.01)
(52) U.S. Cl.
    CPC ...... *C12N 7/00* (2013.01); *C12N 2795/10121* (2013.01); *C12N 2795/10132* (2013.01)

(56) References Cited

U.S. PATENT DOCUMENTS

| | | |
|---|---|---|
| 2009/0232770 A1 | 9/2009 | Krish et al. |
| 2013/0323209 A1 | 12/2013 | Sung et al. |
| 2015/0306159 A1* | 10/2015 | Yoon .................. A23K 20/195 435/235.1 |
| 2017/0189460 A1 | 7/2017 | Shin et al. |

FOREIGN PATENT DOCUMENTS

| | | |
|---|---|---|
| KR | 20150118835 A | 10/2015 |
| WO | WO 2018/208001 A1 | 11/2018 |

OTHER PUBLICATIONS

Richards, G.P, "Bacteriophage remediation of bacterial pathogens in aquaculture: a review of the technology", Bacteriophage, 4(4), 1-12 (Year: 2014).*

Stalin, N. et al., "Characterization of Vibrio parahaemolyticus and its specific phage from shrimp pond in Palk Strait, South East coast of India", Biologicals, 44(6). 526-533 (Year: 2016).*

Office Action dated Dec. 15, 2020 by U.S. Patent Office for U.S. Appl. No. 16/064,725, filed Jun. 21, 2018 and published as US 2019/0000897 dated Jan. 3, 2019 (Inventor—Yoon et al.; Applicant—Intron Biotechnology, Inc.) (8 pages).

Notice of Allowance dated Feb. 3, 2021 by U.S. Patent Office for U.S. Appl. No. 16/064,725, filed Jun. 21, 2018 and published as US 2019/0000897 dated Jan. 3, 2019 (Inventor—Yoon et al.; Applicant—Intron Biotechnology, Inc.) (7 pages).

International Search Report and Written Opinion dated Jun. 7, 2018 by the International Searching Authority for International Application No. PCT/KR2018/002734, filed on Mar. 8, 2018 and published as WO 2018/208001 on Nov. 15, 2018 (Applicant—Intron Biotechnology, Inc.) (Original—8 Pages// Translation—2 pages).

NCBI, GenBank Accession No. JQ692107.1 [Retrieved on: Oct. 9, 2019].

NCBI, GenBank Accession No. JX556418.1 [Retrieved on: Oct. 9, 2019].

Office Action dated Jan. 6, 2022 by U.S. Patent Office for U.S. Appl. No. 16/471,051, which was filed on Jun. 19, 2019 and published as US 2019/0328803 on Oct. 31, 2019 (Inventor—Yoon et al.; Applicant—Intron Biotechnology, Inc.) (23 pages).

* cited by examiner

[FIG. 1]
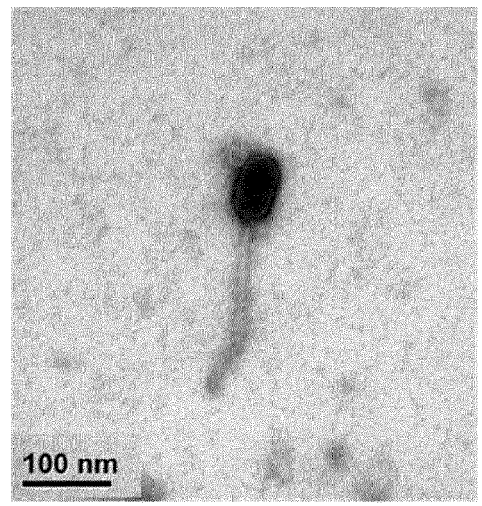
[FIG. 2]
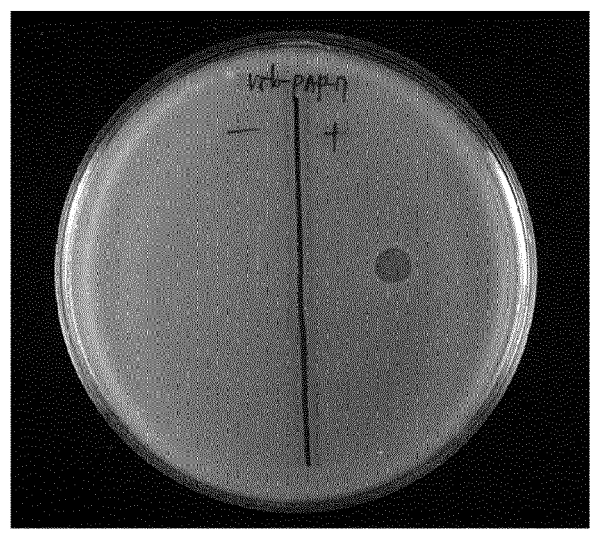

SEQUENCE LISTING

<160> NUMBER OF SEQ ID NOS: 1

<210> SEQ ID NO 1
<211> LENGTH: 76187
<212> TYPE: DNA
<213> ORGANISM: Bacteriophage Vib-PAP-7

<400> SEQUENCE: 1

| | | | | | | |
|---|---|---|---|---|---|---:|
| aagccccacc | ccgtctgggc | tgggactcca | tcggagtgcc | ggacggattt | tgtctgccac | 60 |
| gtgttgggga | ccacgaccaa | cgaccattta | ctaatggacc | tcgaccacga | ccaccgggac | 120 |
| caccggacaa | tgaccgttag | taaatggacc | attggaccga | agggggtttgt | aaattatcat | 180 |
| gggggtgtcg | tatagttcgt | ggaccaattt | tttccgggac | cagttttgaa | gtttttacta | 240 |
| aaacggagga | ccagatgacc | agaccgaaga | ggagattgat | tgtagtcgag | gaccgatgct | 300 |
| tccggggaca | tgcccccatt | cgaattgtgc | ggggctctgc | gaaggcttcc | gtatgctatc | 360 |
| aatgtcatcg | tatgcaaaga | aagcacgcac | gcatggtagc | acgctgccac | aacccaaagg | 420 |
| acccaaggta | caagaactac | ggagggcgcg | ggatcagcgt | atgcccagaa | tggcgtaact | 480 |
| catttactaa | atggtatgag | gacttcggct | acctcgtaga | tgggaatgac | ctgactatgg | 540 |
| accgtaggga | taacgatggg | gattacgagc | cggggaatat | gcgtgcagcc | actacccaag | 600 |
| agcaaaaccg | caatcagcga | agaagtgttt | tactaacgta | cgatggggag | acgctgaatc | 660 |
| aacaggtgtg | ggcagatagg | ttcggctttc | ataaatccag | tatacagcga | cgccttggtg | 720 |
| ggaagtaccg | gaatgatatg | gaatgggtac | tctttggcgt | acgcactact | attactaaaa | 780 |
| cggaggtgct | gattactaag | gacaggaagc | ggttgaactt | gcgtgcttgg | tgtagatcgc | 840 |
| tgggtttctc | actacgcaca | gtagaggacc | gggtatacaa | gttcggctgg | agttatgcgc | 900 |
| aggcactcgg | ctttgcctcc | cggaagggaa | aacttagacc | accgcctaca | aaggattagt | 960 |
| aaataacagt | tgcagttagt | aacactgtgg | catatactct | ttatacacca | actaactaag | 1020 |
| aaggattagt | aaaatgaagg | acttcaatat | gagcgaggag | cttactcgcg | tacaggctgg | 1080 |
| ctggtatgag | cagtctaagg | acgccgtgta | caacttgaag | gatgttacta | agcactcac | 1140 |
| agacggcaag | tcgctaaagc | attgtaagcg | catggtggaa | gacatccccg | gtattggtct | 1200 |
| ctcccaacgt | acgcaggaat | atttgcaggt | ggctttgaac | tgtaaacgca | tggagaactt | 1260 |
| tagtaaatgc | ttgttcaagg | cttatcaaat | tcaaacgcgt | aatgcagcaa | gtctgaagaa | 1320 |
| ggactcgtag | aatggttaaa | ccgacacacc | gcacactggt | agtaacttct | aagggtcgtg | 1380 |
| taccatacga | tgagaagcat | tactaccaca | ctggcaaaaa | gggagaggat | gttacgttag | 1440 |
| taaacgagcg | taacttcaaa | acggtacagg | gacagcgatt | cgaccttgta | cttttcgttg | 1500 |
| gcaacatatc | cggggaagtt | cgtacgaagt | tcgctgggtt | ggttggagat | tattaaaatg | 1560 |
| aaacgcaagt | acttcgacga | agctttacca | tcgttctttg | tgttcgggga | gcacgctaac | 1620 |
| ggtacggtgg | acctatcgtg | cggtgagttt | gatgtagtaa | catactgccc | tacagaaatg | 1680 |
| gcagaagccg | tcatcgctta | ctacgacagc | ctgctgctta | agctgcatga | gtgggtggtc | 1740 |
| gatcaggaga | aaccctcgga | agccctcgac | aaactctgtg | acgcttttcca | agatgttcac | 1800 |
| gcggggcacc | attacatagg | cgacttcggg | gctgtgatgt | tactaaaact | gctatgggaa | 1860 |
| gcgtacacca | aggtagcgcc | aatcgtccag | ccgagattct | tacgtagcgt | gtacggtgta | 1920 |
| gagtggaccc | cctcactggt | gcaagcgaac | ttactaacgc | aacgtgggta | cacccttac | 1980 |
| tgtggggtc | gtgactgcaa | gtcggtccct | cgaacagcgt | tccggagga | gcagttccgc | 2040 |
| tgccctagct | gcggttggga | gtcgaacttt | gaccctgagt | tcattgctgg | gtacaagtac | 2100 |

-continued

```
gtgtgggact tgccgggagt tgactgcgag atgctagacg agttccgtgc aatactacca    2160
ctatcactac acttcgtaat ggtagacgcg gacatgagat acgcggggcg cattgatgat    2220
gagtaggaag cgtttacctt tagtaaaacg tacaagcgta cattgggctc agctcaccgg    2280
gattgtcata atggacccgg atggatggga ccgccagaac ttcgaataca gctggtatga    2340
agagaccatt accattctgg agttctggga tcgcgtgtac aactcaacaa cactcatgaa    2400
attggagaat tagtaaaatg gcaaatacta tcgacctacg cggtaacgaa cagagcgtta    2460
cccgtgaaga tgcggaagcg tatgcagcag ctttgggatg cactgcaatg tacttcgggt    2520
tcgatccaga gcctaaagac gtggacccgg ctatggctgt aaagttcgga ccggaaaacc    2580
cattctttac taaggatatg gagaagttct tgggaccgga tgggagtcag ttcttttaca    2640
acacggcgat gtatcaatgc cgtaagacgt ggagccttcg tgcttaccac ggagcacgca    2700
gcgtggagaa gcttcttgtt aatcttagta aaggttctcc gctatcggtt atggcagcat    2760
acgttgactg cacgcgtatg ctaggtctgt gtgaggaagc ccagatgagt gtattcatag    2820
cacgccagct ttgcatctgc aatcgtgacc gtaagcacgt ggaagaatgc ttactgaaag    2880
cacaggagca ccagatgtcg tacatcgaac acctaaaagc gaaagcttcc ttgatggagg    2940
attagtaaaa tggaaagttc atttggttgg aaccgcgtat tactcgtagg cgggacaaac    3000
gcgggcacgt tcatgggcgt gcttcgtgac cagcaggtgc tacgtatgga gaagaaagac    3060
cccaacgtac aacgccttgg aacacacgtc ctacaacgtg agcaagcccc ggatgaaaca    3120
ttcgataccg aggagtacgt agccacagac cacgccttac gagggactac gatcttcgta    3180
ctgcgaggaa tggctggtgc agacatcccc tgcgagatgt tgaagatcat cgctaagctg    3240
gatagtaaga ttggtgagct aaattctagg atggagcttg ctaatatagc cgcgatgaac    3300
gttgctcact acgtgaagag agaccaataa tatgcgtatg accactatag cgtgtgcggt    3360
taagatacac taccgtgtcc cggtattgcc ggagatgccg atccttatcg ggaataccag    3420
agcattcgtg cagggtcgtg ctgctggtag tgggtttagt aaccgcgtcc actacgacgt    3480
gtccatgccc aagtttgtac gctcagctgc tacgcaagca ttcggacgcc ttaccgcgca    3540
gtttaaggaa gccacaatag atcttacgga ttatcaacat gcttggctgg aggtgagccc    3600
caaatgagcg tagaagctgt tttcgagcag gacatgcagt tagaccctga tatacgcaat    3660
agcaacgttg caggggcttt ctgcgtggct aaagcgaacc tttgcaacgc ctgtcagtgg    3720
gacggtacta tcgacgctac tatgatggtc ctgttattca tgggcgttac taatttcgac    3780
gacgatctga taaagcgttc tgtcgagctg ggctacttta gcatcaaact catgggtatg    3840
gttgacccta tccgtgtgaa ccggggcgat gtgctcgtcc gatcatctac gagcttcgtg    3900
gtggtcacta acgaagagta caatcgcatt tttactaata tactgctata ggaggacact    3960
atggctccct tcttcgtttt cgcacagaca gcaaacacga tggttaatac atgccgtcgt    4020
ctgggcatct caccaacaga accacgcctt atccgtgagc cggagaactt aaagggtgtg    4080
agctttccca aggtgggtgc taaatacatc atcttcgtct gcggcgagac tgtaccactc    4140
tggctgcacc aatttgctgt gttaaataac gtattgctgc ttggcatgga caagcacgtg    4200
atcgagtact accgtaagca cgacttccga gcggaagact acaacgcgta ccaataatag    4260
accgtatagt ttactgcaac atccatttta ctaaaattaa aggagctgac aatggactca    4320
cgttacacat ttatcgacct agttaaagac gtattcgcgg cacttaaacg cgctaaagcc    4380
aacggtgtta ctttcaaagg gcaatctccg tccgctgtag cggctgacat ggcgaagtac    4440
```

-continued

```
gacgctgacc tagagagtgc cccggtagaa gacttggaaa aggctgtggg gcttgtgcag    4500
agcattgacg gcacgtttaa gtctggtatc gaagagaagc tagactcaat cctagcgccg    4560
tcggctgtgg tcatgggctg cgacttcgac gacctgctag aagatacgga agtggcttac    4620
tgcgtcgatg caaacctaga cctgctgacg gttggtgcgt acaatgccaa aggcggttgc    4680
tgcgagtgct gccgccctta ctaccgtgaa tccgtctacc tactacgcgc tatctgtatg    4740
cgtactggtg atgatattac taaaactgtt ctggaccgca aagcggctaa gaaccaagtt    4800
ggagacaagc aataatgcaa gtaccagtta acattacagg tccagtggga tcacttgccc    4860
tagagtacat cggcggtaac gctgataagg tgattgagtt cgttaagaac tgcaccggga    4920
acactccgac gtttaaagag cctgacgtgt tggagtaccc agttatcggt ggtacgcagc    4980
tgatcaccgt tggcagttgg ttggtgtggg ataccactaa actgcactgc atggatgaag    5040
tttactttag caagaacttc acgatcatct gggaacatcc acagcagcct gtcccggtgg    5100
acgagccaga aggtcgtgca ataggctcat acgcgatcaa ccactcgact atcgctgaag    5160
acttggactt ctaccaccac aacgagtttg gcacgcgtaa ggtacgctgt atcaagtcga    5220
actacggtgc tgaaggtcat ccaatctacg gcttactaac tctagtttgg ctagacggtg    5280
atgtggctat gtcgatgcct gttggtgagc tgggagacac agacgagttc tcaatggatt    5340
acctcggcgc ggtagaagct gctaagcagg acatcgcgt gtgtcgtaag ggttggaacg    5400
gcgctgacat gtgcctagtg tacgtaccag cggcagacat cccaacgaag ggaacaggtc    5460
ttaccccgtt cttcggtgat accatgccca tgcgtgctca ctggttacta aaaaccgcca    5520
caggcgatgt agccagctgg tccccatcga cgtcggatag tctagcgacg gactgggaaa    5580
tctactcacc agaataattt tactaaaatg tattgactat aagaaacagg gggaatatac    5640
ttctccctgt tgtcgttttt actaaaccaa aaaaggagtc caacatggat aacgttatgc    5700
cacaccctat gccaatcact taccgccgtc ctgagaaaca gcgccacgcg gtacagctta    5760
ctaagaacaa cgtgggaacg gtaatccaag ccttagtcca ccttgatgtt ctggaaaacc    5820
tagtaatggg tgaggagact accgatccgg gctttggtcg ccgcgaacgt gtcactaaac    5880
cctgcatcac attcacccct aagaaggcgt tttacaagca gttcccggac cgctacaaca    5940
gtatcgacga tggtgaggta gcgatctttg aagacgagta cctagtcttg tttggtaacg    6000
gtgatttcca agtcatgtcg gcacaagagt ttgaagccac ttacaagtgg ggtcaggacg    6060
agcctgcgcc gctatcaccg tgtgcggctc cagcgcaaga tgacttagcg tctattgccg    6120
gggaccgcga gttctctgag cctcgtgtag ctgctctgga gccagaggtg gctattgctg    6180
tggaagagga gatggaagac cttgccgagc ccattgaaga gccagaagag tacggcatcg    6240
aagagcgaga ggagtctcct cgtgcaaagc gtatggctaa gcgtaatcgt cgtgactagc    6300
attgctagta cgttttttact aatctaataa tcaggagaag agttatggac tctactttac    6360
taacagtaac accgaacaag cccttccgtg ccgtgcagta caacggtagt aactgggcgc    6420
aggtacgtca gtttgctgct aagtttgcta acgtagaaat cgcgatgaac ttgaaagccg    6480
acagcccact acttgcgcac cttggcacag gcaatatact catccctaaa gggaactacg    6540
tagttgcttg gggcaagtgg gacctgcgca cgtattcgcc ggaagagttt actaaagtgt    6600
ttgcgggcat tccgtcagga cgtgaccaac tacttgaggt cgagatggac aatgaccgta    6660
tcgtgatgtc tattggtgtg gaatccatgc gcatgagcat cgagtcgggt caggcagact    6720
tcagcgtagg cggcgcagtc cacgttgcag acgtagacat ctttgggcac gagctgatca    6780
gctacttgaa agctgaagct gaagacggtg gtactccagt tcatcgcatg atcgatagcg    6840
```

```
tagcgttgga agcgctagag catggtgctc acggtatcat cgagttggac gaagaagact    6900
tagagcgaga catctaatgg gcgtagtaac tgtacagcgg accaatccga tcatcgcgct    6960
ccaattcacc ggagataacc acgaagaggt gatcgagttc atgaagcaac gcggcgggac    7020
caccgtaacg atgcagtatg acaatttact aaaaattgaa tccgactgct tcctatcatg    7080
gactatccgt cagggtgatt ggattatcca cgagaaaggg tccgtgtgtg aggtcatctt    7140
cggagacttc ttcccggatg ccttccgcgt tatcgagaac ggaccgctgt ttggtaagaa    7200
ggtggtcatc tccggtactt tcggcaaggt aactcgccac gctgtaaaag acctcctatc    7260
tgctcgcgga gctaaggtgt tcggcagtgt gaacaagttc accgacatat tggtgtgtgg    7320
caaggactca ggctctaagc ttaccaaggc taaagagctg ggaatccgaa tcatctacga    7380
gtcggagatt ctggaactac tctagcactt ttactaaaag cctcctaacg ggggcttttt    7440
tgtgtctgaa gcattgacat gtgaaacagt gggagtatac ttattagtaa aaccaacgag    7500
gattaacaaa tgcgtattat ctgtaaaatg ttcggtcacg acactccgtg gaagactccc    7560
gcgaatgtaa gccctatgtg gactcctaag caagtctccc aagacatcct atccggcgaa    7620
gtccgcgtca tcgacccaat ctataccggg tacatgttcc aaggctacga gggcgtgtgc    7680
tcgcgctgtg gtcatactgt cccggtatat gctgataacg tgccgatcat tgagcctagc    7740
ctagtgccta ccgacgacga agagccactg gaccttaatc gtgaacaccg ccagttgtac    7800
ctattctggt gtgatgttac taaaaagcac gcagatgcac gcctatacct tactggtaag    7860
cagataaagt acctatggcg gtgtatctac aaaattacta aagacaatca taacctgagt    7920
ccgacggagt ccgatacttg taactccatc gtgttctcat attggagagc taagaagaga    7980
ggtagcaaat gaaaaagtta atactggtgt tagcaatcac cacaattgcc gggtgtgcgt    8040
cccccggaacg tctacacaat ttgaagtgtg accagtgggt gtacgaacaa gttatggagc    8100
atggggagga ctacttcgat gccgtgaaag agtgtggcta caaaaagatc cctatgtcgg    8160
acccactaga cggggcgtat cgtgtctaca gcgttggggg tggttactaa tggaagccat    8220
ttactacttc agcgactggc gtcattttg gatgtggctt gactggaact tgtatgctaa    8280
cggcaatcta ttcctgatgc tctgctggtc ttggatcttg gcgtcgagcc taatgggact    8340
ccgtgtcaag ctctggcagg cgctctgtaa catcctcgct gtatgcctta cgtggatgtt    8400
cgtttgttat gtagcctacg gaaccggact ggggtgaaaa aaattactaa aaagtgtttg    8460
acactcatct gaaacaacgt tactatcctc cctgttgaat acatttacta atctactaac    8520
tcagcaggga gtttttactaa aatggctact atcactaatc ttcaaaaagt tatccttcac    8580
gcagttgcta ctatcaaaga ctgcacgggc tacaacgtag ctcaccactt catgcccgct    8640
aatgacctcc actggaccgc ctctcaccag caggtatacc gcgaactacg ccgtatggag    8700
tctgcggacc tagtggacag ccgcgaagtc ccacaagacg gcaagcctaa caagttcgtg    8760
tacacgctga ccgagaaggg taagaaagcg tatcaagaag ctatcgccca cgagccatgc    8820
gactacgctg gtcttaacac ccaagctacc atccacgcgc tgttcccaac tgtagagtac    8880
tacgtggcgt ttttgcagaa gcgtaacgaa gagtgtgacg ccctgtactt ccgcaagtgt    8940
gaagacggtg tgtctaagct ggaagagatt cttattgacc gtcgaatctt gatcctacat    9000
gccgagtgta cgttcgcgca gaagatgatc gtaatgctgt ctgagcagca ggaagcgatt    9060
gagggcgaat ctgaagaagt ggtcaagtag tttactaaac ttaaaggagc gggcgtcatg    9120
cgtttcgaga ctatcaatat ttaccacaag tacgggaagt ggatcggcgg tggtcagcta    9180
```

```
agtagccgca gtttggcgga gctgctttcc gctgcggtaa aacctcacca acgcgtggtc   9240
tcaatggttt accatgagaa ccacggcatc tcatccaact acgacatagt cctagaaaac   9300
cacggggtgc aggtgctgga caacgtgcat gagaaccaca cgtactacgt taacaagtgc   9360
gctaaggact ggcaggagga ttccctgttg aatccagaag ccgaggctac gcaggctaag   9420
ccagcatcac ggtctcgtag aaagtaacta ctaagccctc gcactgccgg gggcttttcg   9480
ttatactcca ccgcaaaaat caggaggtaa taacatggct ttatctaacg tttttgacat   9540
cttgttcgga ggtggtttta gtacaccggg aaacttcgtg gctggagacg tgctcgacca   9600
gatcgttgcc tacaccgaac catcacgctc ggaggctggc agcacgctga catcgctgta   9660
cacgaaatac ccaaacttca agacgacctg taggacggag ctgccaaagc acatgcgtgt   9720
tactagcagt gagatcaaca ctatcttctc acagttggac agcaattcag cagcgacact   9780
ctccacccct gctaatagta tcgcactgaa gtggcttgag cacgtaaacg acagtaggca   9840
actctaatcc gtataattac taaaaacgga gattaacaat gcgcaaagaa gtatcatgct   9900
ttagtaagag tggaaagctc actaaagaca tgaaagttat tttagacata gccaccacta   9960
tcgagttggc aatcgtaaac aatcctgaca agaccgaat  ccaagttatt aaggaaacgg  10020
ctcgacgtct taagcaatca ccccagtacc gaaagctgtg ggcacagtcg atcctaaaca  10080
agtacctaca cgccgacgaa accgtatcca aggcacagca ggacactatc gacagcctat  10140
tctcgctccg gcggctggg  tacaaaactt actaaggaga ttgatgtggg agcacttcct  10200
aacaacaacc gcaaggagtc gaacgactcc ccagaccttt acgttactaa ccacccactg  10260
gctattccgg ggctgttctc ccgctggcgt ccagagagcg gttctatcat ccttgagccc  10320
tgctgcggac tttgccacat ttcggataag ctggaggagt tcggtcacgt agtacacagc  10380
ttcgacatgt ttaactgggg gcgtggtaac gctcgtgaag agtatgacgc tcagtcgtac  10440
cattacggtg agtatgagtg cattattact aatccaccct acaaccgagc tatgccaatc  10500
gtagagaacc tactggagca gaatctggct aagggcgggt atatggctat gctggtacgt  10560
ctggagtttc agacgggtaa ggcacgagcg gcggctcttg agcagacccc tttgaagtac  10620
atcctaccgt tcgcattccg tatcgagtgt gacaagggtg tagtcgtgga ggagctggcg  10680
gacggatctt ttgagacaga gttggagaaa tccccgaact catcaaacta cgcttggttt  10740
gtctgggagg atggttacga gggctaccct actacgatgt acatccacca agacatggct  10800
gagcaaacac tggcagaact tactaataga gaggtttagt aaaatggaaa atattacggc  10860
taagcagata gctgacgaca tcgaagagct gttggagaac gctgctgtgt acatccagcg  10920
tcaggttaat cccatgctct tgaagatgcg tacagagcag tgcatcgacc tttacggatt  10980
tgtgatggat agggactcca cggctacttt cttccactgc aatgtacctg cggaggagat  11040
acgcggtatt tacgccagca cgggcgaggt actgatccgt aaagaagtac cgctaacgca  11100
tggtcgtttg tatccgtcac tggctctggc taagaaccgt gctagtcacc gagtggctaa  11160
ccgtattgag aagctgcgag cgtacagccg atcactgtca acagtcacca cgaacgacgt  11220
cagcaccatc caagttaagt agcgtactct acgatgcaag ggcgtcacgt cttcccttgc  11280
atcgtgctaa agagttgaac gctgtgtaca accgcaagag tgactttttt agttagacgt  11340
atatttgtat gaaccatttt actaagagta agggagatga gaagacgaga gagaagaacg  11400
gctgatcagc ctgccattat gtgggaatgg gaagatctaa aggacaaccc taataaagtc  11460
gtatccgcac tacttacaag ctcgtacctg tactacctgc gcagcgactt acgtcccata  11520
atgcgagacg aagactttga cctatgttgc aaattactaa gacgtagata ccgtgaagta  11580
```

```
acgcacatgc acaagtcctt gatcaagatg tccgacctac gcgccggaac cttgtttaga    11640
ctccgggacc acgattaccc aaccatcacg aaggtggtgg ctgtagaatt gtctctgggg    11700
acgattaacg acatgaggct accaacgcct caacccgccg ttaaaaacgc caccacgagc    11760
cggagaactc gaaataaagc tgctcctagg cgggagcgta gtcgcaagaa ggggttttta    11820
taagatgact atcaccggga cgctaattat cctactcctc atgatggagg cgctatcgtg    11880
gggattctgg gtactatggc gtaagttagt aaaatcagga cgcattccta ccatcaagtt    11940
taataagcgc cgacactggt gtgaccttaa gtacgtctac acgcgtgctg agtggcgggg    12000
gcataggact ccgttcgtat gggttactga gcgggagtat ccgataccag agtttactaa    12060
gaaccacccg gacgagctgg cgacagctgc ggttcgggac tttgttgccc agctcataaa    12120
cgatagtgag ttcgtactag atgccgccga taaagaggag atgttctcgc agtacagtat    12180
ctggcttact aaacatgcaa tgccggacaa cggctacgcg atcatagaag actggcgaga    12240
ccagctaaac ccagcgaagg atggaattga cgatgaataa cgataaagtg aaggaattac    12300
taattgagca gtacggggcg ctattagagg agccaacaga tttctttata cagcctagag    12360
atgatgagtt cttcttcgag ctaaacaaca ctaaggcgta ttcaatccgt aacccgtggg    12420
atgcgagcca gccgaaggtc cctacggtgg aaacctgcgt taccgctttc ggtgagctgt    12480
gcgcagctgc tggcattttc ctaaacgaaa ctgtgcaggg tacggaattt gtgggagacg    12540
gtactggtaa gttcgatttc ctaaaaatcc cagtgcgcgg ggtgatcgtg gctatcacgg    12600
ttatcgaagc tccatcctcg cttggggctg tgcaagttat cggtcagact gcggatcgtt    12660
gctttgctct ggttacggtc taccgcgaag actcacagat aaatagtcag ggcaatgagt    12720
tcatcgctca gactatgaat ctgaagactg caaagtaca cacatgcctg ttccgtctag    12780
ctgtcgctga agaccaagac acgttcccag tgtacgttcc gaagatggtg tcagtgaatg    12840
gctactacaa cgcgcaggaa gccgttgaca accaagctga agacgttaag aatatggtcc    12900
cagtggctga ctttactgag taggtcacta ggcgaaccgg acttccttcg ggaaaccaaa    12960
gccctcacat ctagcggtgt gggggctttt tttgtatcct acggctgaca atttacttaa    13020
cgaggactgc gtatggcaga cataaaggag ggcgtgcgtt cgaaactaga cctatatgaa    13080
gtgcagctag ggcgctgctt ttactgctgt aaaccgatgt ctccgggctc ttaccaaccg    13140
agcgtccgtg ccaacggctt tactagggac cactttatac cgaagtgtga gggtgttccc    13200
ggatttcaca atattgtttt aagttgtaag tactgcaacg agaagaaggc agacaaggag    13260
ccttcaaata aggctctggc taaatacgag ttattactaa gagtaagggc tgtgttccct    13320
gaccataatc acaaagactc ggtacggctt tctcgttgga agattaagta cttttaagtt    13380
tagtaaagga gactatatga gtttctggcg taaagaagag ccagtgatgg acgagaacgg    13440
caaactgatc aaaggcggta tgtttgccca ccaacgcgag ttttgggaat cagagagttt    13500
catcaccgcg ttagtaaccg ggtacggtgg tgggaagacc tttaccgcag gcaagatcag    13560
tatctcaatg gcactggaga atcccggcat accgtttatg tgtgtgtctc cgtcgtacaa    13620
ggtcgctcgt aagacgatgg taattactat caaggaactg ctgcaaggta agcagtcttt    13680
gctagagggt tttagttgga agtacaacaa ggcggattgg gagttcttga tccgatacaa    13740
aggtcgtgag ggtattatct ggatcggctc aggcgatgac ccggacgccc ttaaaggtcc    13800
taacttgtgt gggggctctga ttgacgaacc gttcatccaa tcacgcgagg tattcgagca    13860
gatgcttgct cgtgtccgtc accctaacgc ccgtactaaa cggatcatgc tgacaggcac    13920
```

```
cccggaggac ttgaactggg gatacgacat cactgagggt gaggagaagg agaacttcga   13980
cgtacacttg gtgcaggcat cttcgaaaga aaacaaagca cttggtaagg agtacacgga   14040
acgccttgag cgtggtctta gtgctcaggc tgctgagtcg tacgttagtg gtaagttcgt   14100
accgctggct aagggtcgtg tttactacgg cttcactcgt gagcgtaacg ttatggagtt   14160
cccggagatt cctaaaggag ctaagattgg atttggtctc gactttaacg ttaacccgat   14220
gtcggcggct atgttctggt ctttgaatgg acacatccac ttctttgacg agatcttact   14280
accgaactcg gacacctacg acatgtgtga gacaatattg gctgagtatg gacagtaccg   14340
ccctatctgt tacccggatg ctaccgggcg taagcgtcag actaacgccg ctggcggtat   14400
gaccgacttc cgtataatta gggatgagta caagatcaag attgacgttg gttctaccaa   14460
cccgcctaag cgtgaccgat acaacatagt aaatggcaag ctgaatccta agaagggctt   14520
gcctactatg actatctcac cgaagtgcgt gaagatgatc cgttacttag agtcgtactc   14580
acacgagaaa atgaagcaac aagaagagat gtcccacatc ttggatgcta tgggctaccc   14640
tgtagcgagg atgttcccgc tacacatgcg tgcgggcgtt actaaacttg caggtcacta   14700
aggagatttt actaatggct gaagaaaaca agaaggctga gaaagttaca ttcacagcta   14760
aagagattga gcacaagaat aagatttaca cccagaagat taaacgctgg gagaagaacc   14820
gcctagtgtg tgctggtaca gacgctgtga aggaggctgg cgttaagctg ttgcctcagt   14880
tggaaggtca gtcaaccgac gagtacgatg ctatggtagt tcgtgctaac ttcttccccg   14940
gagctctacg tgccctgcac ggtactaatg gcatgatcca cgccaagact ccaaccatca   15000
cgttcccgga aggcaagatg tcttatttag ataacatcgg tctatcgggc tcatctatcg   15060
cggaagtggc agaggaaatt accgaggagc agatgctcca aggctgggtg ggtatctttg   15120
cgttctacaa ctccgttccg ggtacaagcg agctaaagcc gttcctgtca gtaatccgcg   15180
ccgagaacat ctgggactgg cgcttcggtg tggtaaatgg cgttaagcaa ctaacgtacg   15240
tcaagttcgt tgaatacgtc gagtcccctg actccaacat gttcctatcc gttgagattc   15300
cgcaagtaac tcagctgtgg ttagacaaga atggtaagct taactaccgc attgtgcaga   15360
agcaaccggg cgagcagaag ggtgaagctt catgggtcca aaaacagggc ggtgcagttt   15420
tagtaagagg taaggaagtc gagggagttc cttttccgttt gatcggtgct cgtaagatgt   15480
cgggtcgtcc agaggaagct cctattgagc ctatcgtaga cgtcaacatc tcacactaca   15540
tcacctccgc cgacttggag cagggtcgcc actttaccgc actgccaaca ccgtacatct   15600
gttccgcatc gttagaccca gacaaggact tccgcatcgg tggttacaac tgctggatca   15660
tcccggagaa cgaagccaag gtaggtatgc ttgagtacac cgggcaaggt ctgctttcac   15720
tggagaaagc cgatactgag aagaaatggg aaatggcagt actgggtgct cgtatgctcc   15780
agaacgacaa gaaagccaat gagtctaaag acacggtccg actacgccag acgggtgaga   15840
acagtatcgt tactaacgtt gcacgccagt gttccgtagc actaacctac ctccttggta   15900
aattcattgc cccgtggacc ctcgtctcta gcggtacgaa gtaggcttc gtactaacca   15960 cagacttctt gaccatcgag atctcaaccg agatgctgaa ctcaatggct gcgctggtgg   16020
ctaccgacaa gatgtctatg gaaacattct tctacaactt gcagcgtggt ggtatctacg   16080
aagctggtac tactcttgag aaagagatgc agcgtatcga gaagcagttt gaaaagcaga   16140
tgaagcaact tggtcgtaag agtgacgtgg tggacttaga cgatgaagaa gacgagatcc   16200
cggacgatga gcaggctaag aaggacgaga agaagactgc gactaatgac cacgtagaca   16260
atcaagctaa gagtaaggat tagtaaatgg cgaactttag tgacaatctg gcggtagttt   16320
```

```
acgcagacca ccagattgac ctataccgct atgaagccaa ccagcggcaa gacattgccg    16380
ctttcctact ggcaatggcg gacgagataa gagaggcgtt actaaaagct gacttcggct    16440
cacagccgtt tgttactaaa cgtaaactca atgcgttact aaaagaaatc gaagcaatca    16500
tcaagcagta ctacaaagac gctcgtgact accagctagg cgagctgaag cagttaagcg    16560
taatcgaata cgcttgggct atgtctgcga tgaacaacac cattggtgcc agcctgttcg    16620
agaccttcct tactaatcac ttcctagaga gtgtcgttag taatgtcctg attgaaggtg    16680
ctccgtctaa agagtggtgg gctcgtcagg ctacagacac aatggagaaa tttgtagacc    16740
agatacgtat gggtgtagca ctcggtgaga ctaacgatca gttaatcgaa cgggtgaacg    16800
gcaagttcct ccataagttc ggcaagcgta agatgtctga cggtaaggtt aaacgctacg    16860
gcttgtacga gggtggaata ctcaagacat cgcgctctaa cgctgagact ttagtaagaa    16920
gttccgtgca ggctattgcg aatgatgcta agatgcgaat gtacgcagct aacgacgacc    16980
tactgcacgg ttatcaacag ctatcggtac tggacttaaa acatctgac atctgtatcg     17040 cccgaagtgg tcttgcatgg acggtagagg gtaagccgat tgggaatcac aagaagcgtt    17100
tccgaatccc ccctctacac tggaattgcc gatcactact gttaccgatt ctgaaatcgt    17160
ggcaagatat gccgggtaaa gtgcgtacta gccttccggg aagtatgcaa gcgagtatgg    17220
atggtttagt tagtgctgac cagacgtacg aagatatgct caagcgtcgt acagatgctg    17280
agatcaagaa gaagcttgga ccgggtagat tcgagttgtg gaaacagggt aaactaacac    17340
tacgcgatct caccgaccaa gatgatcgac cattaacatt gaaagagtat cgagaaagtg    17400
cttaaaatac acctcgattt tactaacagt aacatgaagg acaaaacacc atgcttaaat    17460
tccgtgttca gaaactagac gacgtgaaag aagagttccg ccacctatac atccaacaag    17520
ctgacggctc tttccaactg ggtgtagaag gtgcggtgga caaagcgaag gtagacgagt    17580
tccgcaactc taataccaac ctgcaaacag ctaaagaaca gcttgagcag caactccaac    17640
aaatggctac taagttcgac ggtttagacc cagagcaggc taaagaagct atggagatga    17700
tgaacaagat ccgcgaccag aagctaatcg aagaaggtaa aatcgaagag cttatcgaag    17760
cgcgtactaa agacatgctt actaaccacc agacgcgtga gcaagagctt acgaaatcca    17820
ttaaggactg ggaaggcaag tttagcggtc ttcagtcaaa ctaccgtaag ctaaagatcg    17880
gctcggacat ccttggtcag ctagacaaga ttggtaaggt tcacagctca tctcgtgaca    17940
tcattaccga cctagctgct caggtttggc aattgaacga gaaggacgag cttgtggcaa    18000
tgaaaggcga ccagcctgca tacagcccag ccgacgctac taaaccacta tcagctgaag    18060
agtggtgtat gcagctagcg aatgaccgtc cgtacctgtt tgagtcaact acctcgatca    18120
gttctggtca agtggtcaa ggtggtcagg gcgttaaggg tgttatcagc ggcgacgata     18180
tggacgcatt cgagaacaac cttgaagcaa ttgcatccgg tgaagttcaa gtaaacgtct    18240
aactctgaat tttaattta gtaaacataa agccaccttc gggtggcttt tttagtttt     18300 tattaataag ggggttgacg aacttagttg tttgggtttt ataatgtaac catcaaaagc    18360
aaacttggtt agcggcgggg tcgcttctca agggtttcgg ggaaaccatg cgaaagaact    18420
tatcaaacga caacacgagg acttagcact atggctaata ctttagaagc tgtcgccccg    18480
aagctgttag ctcagggctt aatggcactt cgtggcacga acgtaatgcc gactttagta    18540
aaccgcgatt atgatcgtga tcttgcagcc aagggtctga cagtggatat tccaatccct    18600
tcagcggttc ctactcagga cgttgcaccg ggcgcaacac ctcctaacac tggcgacgta    18660
```

```
gcgccaacag tagcgaaagt tacactagac aagtggaaag aagcaccttt ctacctaacg    18720
gataaagacg ttaagcaatc aatgaacggt atcatcccgc ttcaagcgtc tgaagctgtt    18780
aagtctcttg taaacgacgt taacgcggac atcctaggca aatacacttc tgtatacggc    18840
atggtaggta ctccgggcgt aactccattc ggttcaaaca ccaaagaagc aactgacgct    18900
cgtactaagc tgaacatcca gcttgcaccg ggtcaagatc gtcgtttcgt tatggaccca    18960
tctgcggaag gtaatgcact taacctacgc gcattaacg acactaactt cgctgtgact    19020
gctcagcaag tacgtgacgg taaaatggct cgtaaactag gcttcgattg ggcgatggat    19080
caacaagtac ctgttcacgc tgctggtctt tcggctgcgg ctgttaacgg tgcgggtcaa    19140
acaggcaacc aactagcctt cgacggtggt gtagacgctg ctgacggtgg tactggtgtt    19200
aaagctggtg acatcttcac tattgcaggt gacgctcaga cttacgcagt tgtagcaact    19260
actggcgcta aagctggcac tatgaccgtg actccggcga tcaagaaagc tccggcggac    19320
gacgctgtga tcacgttcaa agctactcac actgttaact tggcattcca ccgtgacgcg    19380
tttgcattcg catctcgtcc gctggctgac caaactaacg gcttgggcaa catcatccgt    19440
actgcaactg acccggtaac tggtctagca ctacgtcttg aaatcagccg tgagcacaaa    19500
cgtactcgtt tctcgtacga cctactatgg ggttcatctc tagtacgtcc agaactggca    19560
gtgcgtgtag cgggctaatc ccgtataggt catgggaggt agggttatcc cgcctcccta    19620
tttttttaag tttagtaaac tgagagtacg aattatgagt caaattgacc cgcaagagat    19680
gcttaagcaa atcttagctg catctgataa cccagcagaa ctactacgtg gtgcgatcca    19740
agaagctaca agcggtgaga acggcggcaa cgctcttcaa cagcttgaat tacttctagc    19800
atctgaccct aacctaaaac accacctacg ctctggtatg cctgcatccg tgcaagaaca    19860
cctacgttac gtacctacat tgattgttac gtttactaat ggtgctttcg gcggcaaacc    19920
aatggtgatc aacaagtcgg acttcgacgc tgaccttcac gaagaagttg acgttgctaa    19980
agctgttaaa gcggctgctg cttctgctgc taagcaagaa gagcctaccg tcgatgaagg    20040
cgctggcgaa gacgctacag gcgaaacgga agatcagacc gaagacgctc ctaagcaggg    20100
tcgtagccgt aaccgccgta gctaattagt aataccctatt actaacgtta ctgttgattg    20160
gaaggaggag gcttaggctt cctcttttt gtttctggag attactaaaa tggcaatcac    20220
attaaccgta cagactggaa tctacccggt acgcaatgcc aacgcgttcg cgtctgtaga    20280
gcaggctgac aattaccatg cgcagcgtgg taatacagag tgggcaggct tcgacgccga    20340
caagaagaaa gctgcactga tcaagggtgc agacttcatc gctcaagagt tcaatttccg    20400
tggtcgtccg atgtatagcg aagaagaccc gactaaccca cagttcctac cgttcccccg    20460
ccatgacttc gtagacaagg ctggtcgttc tattactggc acgccggaag gcgttgttcg    20520
tgctaacatg gagctggcat tgtttgccgg acgtgggac ctttacccta accagaccac    20580
attactaaaa ccgggtggtg ctgtgactaa ggttagtaag aagacgggtc cattgactac    20640
tacgtacgag tacgcaaacc ctgtagccgt tctgcactca acaccacact acaagaaggt    20700
gagcagctgg cttaaggact acgtatacac taccgggcgt attcaccgat agggattac    20760 taaaatggct aacgcatacc aagagcagat cgacagcgct ctggaaagta tcaaggaagc    20820
aggcaagcag ttcgacttcg cgcttactac tgtgggcaac aacccggata gccgtggct    20880 aggtggtaca accaccacaa ccgatgtcaa gctgtgggct tgtgtctttc cggttagcag    20940 tgctcccttct gcactacgtg agccgatgct caaacagggc accatgatcg aaactcaaat    21000
gcgctacgtg ctagcagctg gtgaaggcag aactacacac ccaaacacag gtgacgtgct    21060
```

```
aaagtcattt gaggggaacg actgggcaat catggcatgt gcgcctctta ccgttaacgg   21120
ggaggctgcg atcatttacg agatggtagt taaacgatga acgacataga agcacgagaa   21180
cgcattaacc aagaacttac taacggctgg gcgacccatt ctgccacggt tgatattgcc   21240
tacgagggcg atggttacaa gccacaaccg ggcaaggctt atatcgaagt tattttcagt   21300
gtagaatcca cttcaagcca gtcgctgggt gatgagggta atcgctcctt tatccgcgat   21360
ggtgttgtac acgtcaacgt gtacactccg gctaacaacg gcaacgcctt cgcagctcac   21420
atctacgcta tggctgtacg tgatattttc gaaggtaagc atttcgggga cctttggttc   21480
tgggagtgta aagcaagtcc tgccgggaac gatgggacat acaacgtagc gtacgcaaat   21540
tgtgcgttcc gctttcagca aatcaagtag gagaattact aatgagtgat actaaccgcg   21600
tacgtcttgc cattgtggaa gagactacac cggggactgt ccctaacaac cctaagttgg   21660
tacgccagcg cgttactaac atgccgtctc tagcggtaac gccggagact atcgaatcgg   21720
aagaactgga cccgtccatg cagacaaccg acctcatcaa agtaggtcag gctgttggtg   21780
gtgagttcgg tatggagttc agctacgacg ctcagaagca atcaatgatc ggcatcatgc   21840
gtaacagctg gaactcgttc acgcagtaca agggtgatga agttggcgct atctcagctg   21900
gcaaagttgc tgttactaac gtaggcgctg cgctacctgt tggtgcgctg gttctgttca   21960
agaacttcaa caactctgat aacaacggtg ttaagcctgt tacggctgcg accaccacag   22020
atattacagc tacgggctta gtagccgacg cgtctaagac gggtaaggaa gccattcacg   22080
tagttggtct gcaaggtggc tctggtcatc tgactgtcac cgcaaacacg cttgaagcta   22140
cgtcagggtc gaacatcgac tttactaact ttaagctacg tccgggctcc ttgatcaagc   22200
tgggtggtaa ggacgcggct aaccgcttcg ctacggctaa cgtgaacgct atggtgcgtg   22260
ttactaagat tgaagccaag aagcttacgt tatctgacct acctactggc tgggctgctg   22320
acaacggtgc tggtaaaact attcaagtct ggttgccaga ggacgacatt gtgaacggcg   22380
tggctaccaa gtcattcacg ttccttcaat cgttcttgga ccacaacccg gtaacgcacc   22440
agatcttcaa tggtatgcgt atcggtacta tgaacatgga gatgcgttct aagcagatcg   22500
ttacgttcag catcaacgct cagggtacta agggtgctat cgacgagacg ggtgtggcgg   22560
gtgctactat cctgccagcg tctacagacg tggtaatcaa cacctcgtct aacgttgcgg   22620
agctacgcga agctggtcgt aagattgaag gtccgaacta cgtgacaggc gttacactgg   22680
cgctgaacaa caaccacgt aacgacgacg caatcggcta cgagtctccg gttaacatcg   22740
gtggtggtac gttccagctg acaggcacgc taaaacgta ctttggcaac aagtcgctag   22800
ttgagaaggt gatcaacaac tcgacaacgt cactgctcct aaacttcaaa gacggtgaag   22860
gtcagcacgt ggtgttcgat atgccacgcg ttaagtactc tagcggctct ccggcggtat   22920
caggcaagaa cgcggctaat accgcagacc ttggctacac ggctctgaaa cacctagact   22980
acggctacac gctaggcatt cagaagttcc gttacatgga gtaaatcgaa gcacttgcgt   23040
cgaggcacaa cctagaataa gatcaaagcg tccaatacgg gcgctttttt aatattagta   23100
aacaaggaaa tcccatgaag aagactaacc ctttcgctct attccgcacc tctactaacg   23160
acgaagtgaa cggcgtagtg gtaaactacg gctcattccg cgttacagtg gcgtacgctg   23220
gcggcgctaa cacagactac aaccgtctgc ttatgaaact tggtaagccg tacttgaaac   23280
taataaagtc aggcaacctg ccagaagaag ttacgaaaga gatcgatgag aagctttaca   23340
cgcagaccat catcaagaac tttgaagtag acgtagctga agaaggtgca gaagctccag   23400
```

```
tgtggaaacg cggcattcca actgaagaag gtgaagtcct agactacaac gaagagaact    23460
tagtaagcct actacgctcc cttccacacc tattcgaaga cattaagtca ttcgctcagg    23520
atatgtcgaa ctacaaacct gatctggaag tagctaaggg aaactaatag agtttctaaa    23580
gcatgagctg gaatacgggg acgatgattt cacgtttatc attgaagccg caatcgaagc    23640
cggagaccca cttccggctt tgcttcaga agcgccgaaa ctcctagacc cattagtacc    23700
aacctataac atgttctggg atatataccg atacagacgt gttatcgcca gaaatgattt    23760
tgtcccttgg gaagtccttg aacggttcgc cgctaagtac gggattgaag agctgggaga    23820
gtttcaagag ttctgtgagt tgttccgcga gatggagaaa gtttacttag accacctagt    23880
agaacagtac gaacaggaac agaagcagga ccagaatcaa caaggggac agcatggcga    23940 atttctcgga catacctaaa gatctaaagc acttcgcttt caccctccaa gctaataccg    24000
aaacaaggca gcgtgaagtt gccttgacca ttaccagaga gcttatgcag cgaaacccta    24060
agaagacggg tcgttctgct ggcaactggc aggtcggtat gaatcgcccc aaactaattg    24120
cacaggctcc tccggtagcg gagagggctt cggatgaaga acttagtaaa agttctaaac    24180
tgttcgtgca gaaacaactt agtaaagcga ttaacgatat tactaaggga actctacgcg    24240
gggatgaccc ggtaatctat attagtaata ccatcaacta tgtagtttac ctaaacacca    24300
cccgaccatc accacaggct gctccgggct ggattgaagc atcgatccga tttggcgcag    24360
atagcactaa gggagtgaaa cttacgtaat ggctggtgaa agttacatta tcaaggtacg    24420
gcaacacggt gcgcgggagg tcaaacgatc actcgatgac atcggtgcta gtgctaaaca    24480
gaccacgagc acactggagg ggatgcgcaa gggcttgaac ctcctactgg gtctctacgg    24540
tctaacagca ctacagcagt atgccgacga atatcaaaac ttggatgcga agcttaagat    24600
cgcaacgcat agtacagagg agctggctcg tgcagaggac cagcttttcc gcattgcgaa    24660
cagaacgtat tcctcattct caagtaccgt tgacctatac gcacgttttg agcgttctac    24720
acggagtctt aagatctcgc aggataaacct cctacagatc acagagacgg tgaacaaagc    24780
cattgcctta tccggtgcaa gtactcaggc tgctaacgcg gctatcttgc agttaggtca    24840
gggtatggcg gcaggcacac tccgtggtga cgaacttaac tcagtgctcg aacaagcacc    24900
acgtctagcc gaggcaattg cttccggtat gggcgttgct gttggtaact tgaagcgtct    24960
tggtgagcag ggacttatca caacggaaga agtactcaac gcacttgcgt ctcagggtgc    25020
tgctatcgac aaggagttcc taaacgtaaa ccttactatt ggtaaagcaa tggaggttct    25080
gaataaccag atcctacgtg ccattggtca gctagatagt aaactaggca tctcgtctac    25140
catcgctaag tctattgtaa cgttgagcca aaacctcgac caagttgcag gcgcggctct    25200
tggcgctgct gctggtcttg cagtaatgta cgcgccagct ttactaaaag gtctggtaac    25260
tgttacgcga ttagtaaaag ggttaactct tgcgatggtt tctaacccgt tgggtgcgat    25320
ggcggtagct gctgccaccc ttatcggcta tttgaccatt atgggcgacc agattaagcc    25380
tctgagcgat agtttcgcta ctgtggcgga cttcgctact gctggcttcg atatggcgtc    25440
agaatcgctc tcagggcttt acagcttaat tgaggatgat gtcaattctg cactaagcac    25500
catgcgtacc acagcagacg agctgtttac taagatggga ccgttaatcg accaagcaat    25560
gtctatcggt tacgacgcta tcaacaaagt gatcgggcg ttcgttatcg ctcgtaaggt    25620
cggcgctcaa ctgttcgaat tagtactaca gggtgcttcc ggtctatggg agggtctaac    25680
agcattctac gacttctctg taggcttggc taagtcgatg ttccagactg tcggcggtat    25740
tgcaaacaca gtgtcgaaga gcacgggtat tacactggag tcgctggcac aaggcttcaa    25800
```

```
gcaggttctt aacatcgcta tcggtgtgtt cacgttaatt ccgcgcctag catttactat    25860
ggcgaagaac gtagcgaaga acttcgaggc actgtttgca gatattacta atatgggctc    25920
ggctacaatg gaggctctaa aagtagcgtt ctcaggcggt gactttactg aagcgttcaa    25980
caagatccga gctcagtcca acggtgcgat ggacggtatg ggtgacgaca tatctggcgt    26040
tctaaaggac acgttcaatc aagactacgt tggcgacctt attgctaaga ctgtcgagtt    26100
gaaagagcag ttcatggata cgttcggtga tgaccttgct caagactacc tgagtgacgc    26160
tcagcaatct ctaagcgagt tctacaagga gttcaagaca cgtgctgaag atgcagctac    26220
tgcacgccta gcggctgagc aggaagttac taaagagtac gagaagcaga acaagattgt    26280
gggcggcggg gatgctttca gctccgacca gattgataag tttactaaga agcttaacgc    26340
tatgcgtgag actcttaacg ggctcgaccc aacttgggaa cgctcaactg agatcatcaa    26400
catctggcgt gatacagccc ttaacgctgt agacaagaac tgggagcgtt acgaagagta    26460
cgcgaacatg gttgatgaag ttacacgcga gaagatcaac aaagcctact gggagcacat    26520
ggaccaatct gaggctgctt tcgatggtat gatctcagcc gcgcataaaa tgcagaagga    26580
gtacgacaac tctgctgaac tcatgaagaa aggcatgggg acggtgattg acggtcttac    26640
taaccagttc atgcgctttg ctatgactgg taagtttagc ttcaaagagc tggcggctgg    26700
cgttgcttct tctatcgctg aaatgatgat gcgtatgctc gtcatgcgtg cggttctggc    26760
agcgttgaac gtaattccgg gctttgctgc tgctatggct ggtgccgacg ttgctggtca    26820
ggctgcaacc gctggcggtg ctgctgccaa cttcgctaca tccaccgctg ttctccagca    26880
aggtatgggt caggcacagg ctgctaactc gaagatgtac gctaagggtg gtgctttcag    26940
tcgcggtgtt gagatgtttg ctaacggggg tgcctttact aacagtgtgg tatctcgacc    27000
tacaaacttc gcaatggctg gcggtcttgg tatgatgggt gaagcgggac cagaggctat    27060
tatgccgcta tcgcgtggat ctgacggtaa gttgggtgtt caagctagcg agccgcttc     27120 tccagaggtg aatgtgttct ttgtacaaag cgccgatgaa gctgcggaac taatggctca    27180
aaacccgaaa gcaattaaca aattagtaag agcaattgac gaggctaaag gataactatg    27240
gcacaccaga aaggtacagc caccaactat aaggacttct tatctaagct ccgcacgttc    27300
gctacggcga acgggtggac ccagaagaga tggagcaatc cagctagtgg tgagcatgaa    27360
ttaatcctac agtctgtggg agactcaggt agtgacgcta ttacgttggc gtgggcaacg    27420
cacaccaacg cggatactga tattcacaac attcgatgta aggtagggaa taccttcgtg    27480
gataacccgt tcgacacatt agtaaatacg aactcagaga cggttgtgta cttatggaac    27540
gggtcaattg actaccacat catggtcaac aaagagcgga tcatgttcgc gtgcgctgta    27600
tccggtacgg cgcagtacta ttatggtggc aacttccgaa catacacctc taaagggcac    27660
tgggtaaacc cgctatgctg ttttggggtg ggtactaaca aggatggtcg ctggtctagc    27720
actggcgatg actactctgg ctggcagtac gtacgtggta ctaaggctac tccagtgtat    27780
aaccatgaga aagtgtggaa gaagatgtca ctcatccacc ctttcatgga taccactaac    27840
taccacaggt acatagagta cgccaatggg gatcgcgcac tactccaagc aatcattcag    27900
gttgagggta tgcaagtagc gggtgagctt atccgtgtgt tcgggactgg tggtatcggg    27960
ctgtcgaact tccaagagct ggtacatagt aatggtagaa gatatgttgt agtgcagaat    28020
gtgtaccggg cgtctgctgg cgattattta gtaatggaga tgagttaaat ggcttacgct    28080
acagagaact acgggtcgga gcgatcagac ctgatagctg cgatcaagaa caggttcgaa    28140
```

```
gctgctggat tcaccatcgc acaccaccaa ggggaggtgg tgattataca attacaaacc   28200
aacctatttg tgcagtaccg ctgcatcaat ttcttgtacg ttacgcgtcc cggacgccat   28260
agatacacaa actccctgcg ctggcgtatg gggactgggc actctaatgg gtcccttact   28320
aacgctagtc cagaagaggg tatgggatct ggctacagcg gcttcaatgg tccgatccaa   28380
cacgttccct taccgggaaa actccacttc tgtaaaacag acctagcggg caaatatgat   28440
tacgtgcttt gcttggagaa taccgctgac gctaaaggag cctcgtgttt agcagcagag   28500
cttcaatgtg tggacgctga gtttggtgat cgtagccacc actacttagc gggaaatgcg   28560
acgagtggta gtaccgtgga gggtaatccg ggaccgttta ttagtgctgg catgtacacc   28620
ggagggtctg ggtttatcgc taggattggt gccgacggga acctgcaagc gtacctgccc   28680
gctagtaccg agcagaatta caactctacg taccccacgg caaacagctg ctgtcggta   28740 ggaccctacg gatactacag gaccatacag gacaagttgt acttcgaccc ctcccttacc   28800
acgatcatgc tccccgctgt ttgggggttgc cgtatgcccg ctgcctctgg gaactatggg   28860
ggaccagtga agggcgagtt ccgcaattc aagataacca cgatgaaata cgcgggcatc   28920
ggcacagaga tgacgctgga tggtaagaag taccgattgt tccctaggat tggtaagggt   28980
ggtgagaaca cgctagccta cgccattagg gagagttgat atggcagcag ttcgtatctt   29040
tggtcagggt gtgggctata cgctcatacc cgaaccacca ctcccaacgg aggtcaaggt   29100
agccttggcg ggcagtactg acgctgttct acgcacaaca ccgcaggctc cgagcaactg   29160
ggcgactagg aagcaggatg gttctgtggg gtacgtagct gacggacctt ggagtttact   29220
aaaaaactcc atattcatgc agccgaagtc gattgacttg ggtcttgttt tgggtccaag   29280
tactcatgcg gtgcggatct ggagtcttta cgaaaatgcc ataacttctc cgaccatcac   29340
agtcacgggt ggtactggta tctcgcttac aggaactacc agcaacgtca cactgcaccc   29400
atacggcggg tttgctgact atacagttaa cgtgtcgcta gcggtatctg gaataatcga   29460
cgcgaagtac cagtggaact tcaatggaat accagcttct ttgcagacgc tgagtatcac   29520
tggtcagaga atcgttgtat tcgggatacc accacaacga cgcgtaactg agaagcttag   29580
ctggaggact gacgtgatcc gagcactcga cgggtcagag cagcgtatcc gtgtgcggga   29640
gaatccttta gtaaatgtgc gcttcaagtc agtaaccggg tattacgata cacagggtgc   29700
ggaagctatg ttgtacacac tagggcacga cgccctagca ataccagtat ggcacgagag   29760
tgtacgtact agcgtgaccg ttccagctgg caccactgag atgaacattg acactactgg   29820
ctctacgttc aaagtgggtg acttgcttat actatggaag gggttctacg agtacgagac   29880
gggcgaggta tcggctgtta ctaatagtaa aataacgctg aagaagccaa cccgccatac   29940
ttgggataag cctatagtag cgcctctgtc ttacggtctc atagattccg taaacttcgg   30000
caagtacaag ataaacgtgt ctgataactc agtcgagtac acccgcaacg ccaacttcga   30060
aataccggag gtgggcactt acccactgta cgacgggata ccagtatacg gagagttgtt   30120
ataccaagct gggaagagca gccctaacac ctacaagccg tcggtacaga cggtggactt   30180
cggtattaag gctaggtctc agaagaagct atttgagttt ccagaagtca cacgcgagat   30240
tttagtaaaa atgaatagcc gcaggaagt tctaaaaatc aagaagttcc tgtcttactt   30300
aggcggcaag cagaagccat tctggtatgt aagccactgg gtggatttct tgcctactgg   30360
ggttactacc gttaatactg agttgcgtgt acgggatatt ggtcttgttg agtactacgc   30420
ttcagcgcct acgcgtaaat ggttagccat taagcctagg gacggtgact gggtgtatcg   30480
tcagatttcc tctgtagcca agggagctac tatacaggga gtacctgcga acgaggtgat   30540
```

```
cacggtagac accgcaatac cattcgcttt tagtaatgag acggttgaga aggtgtgtct    30600
aatggtccca gtgcgattaa cacatgacga tgtggtgttt aactgggata atatgcagca    30660
catcacaact aactggaagg ttctggaggt tactaaataa tggcttacca agataaagag    30720
gacagcctct acgatggtcg cccggtaacg gcataccact ttgagtacga cgggaagagt    30780
tattggtaca cgtcttcgga ctcggatata gcctctcccg gtggtgttgc aaagagtgtt    30840
cacattaagc acgggcagct gaaggagact accgaggata agcgatcaac tgttaagatc    30900
gagattgacg cagacacgga gatagcgaaa gctctccgtg ttaatcccgc agactctgtg    30960
tgtaaggtta gtatactaag atctcaccgc aatgatgcag ccaagcagtg ggtgtactac    31020
tggcgtgggt ctgtctctat cgtcggcagg gaagatgccc tccagcttaa cctagaatgt    31080
acccacatgc ttactacgct ggcatctggc ggtcttcgtt ctcgatacag ttactcatgt    31140
cctcatgcgc tgtacggtcc tagctgccgt gctactaagt cctcagacaa ggagcgtgac    31200
tttgttgtta cggcggtatc tggtgctaag gtgtccctgt ctgggtgggc aaacactact    31260
tggtggaacg gtggtcagct gtcattcgag aataaaaagt accgccgtta tataatggct    31320
gctgacagcg gggggatact cctagacgcg gtcccggtag ggttggctgt agggatgact    31380
gtgacgttaa ctgccgggtg tgaccgcact aaggctacgt gccagtctaa gtttaacaac    31440
ctagctaact acggggggcta cctagcagtt cccaacaaga acccgttcca agacgggatt    31500
gcttaatatt agtaaaagga gtaattatgg ctgttcagct actctggtac gcagtaatac    31560
ttatcgtatc agtgattgtg tctgtagccc tagcgccgaa gcctccgaag cctgactccc    31620
ctcagactaa ggatattaac gcgcctacag cttcagagaa tgagtttatc ccagtagcct    31680
tcggcaccac ttggctgcaa aagccaaacg tctgctggta cggcaatacg gggaccgatg    31740
aaatccgtaa gagtggaggt aagaagtaat gtccgatagg gtggaactgc tccccggcga    31800
agaggacttt agactataca tagcggactt cgatcaggag tccgttaaac agttcaattg    31860
ccatagcggg atgcgtgcca aaggcaaagc ctacggctta gattggtggg attttcttac    31920
taatggaatt atgttctcag agctggcagc tcttgaggat ggtcagatta accgatgctt    31980
agtggagatt ttaaatgggc ggaggcggaa gtaagagcca agtcgtcggg tacaagtact    32040
ggggtgctat gcagctggta ctctgccacc gggggcttga gtcgattgat agaatacgcg    32100
taggcgacaa agtggtatct agtgaggtga tcacgcagtc caactgtcta aagtacatcg    32160
acaagtggaa cacgttcggc ggggacaagc gtgagggtgg tccagtggga ttcgcacgct    32220
tcttcttcgg gcacgatgac caacctgtta gctcgcttac tgagagcatg taccagagcg    32280
gtacagcttt ccgtggtgtt gttagtgtgt ccctgcctaa gatgtacttc tcagcaaaca    32340
acccgtacat aaagccgtgg tcattccgtg ttaagtcata tccagagact ccgggattag    32400
taagaactca cgttaagatt gatgctggta atggtatcgt aaacatgaac cctgcccaca    32460
taatctacgc gtgtttagta agtcgtagtg accgctgggg actggggctt gattacacta    32520
aggacataga cgtaccttcc tttgcttcag cggcgtccac actccactca gagaagtttg    32580
gtatgggcat cgcgtgggag aacaactcag gcgtagacga ctttatcaaa gagatcctac    32640
gacatatcga cggagctatc tacgtggacc aagtgtcagg taagttgaag cttcgcttat    32700
tccgtggcga ctacaccgtt agtaatttac cagtactcga caagactgta gttaaagacc    32760
ttgagaagtt tgagtatccg cagtgggggta acataaccac gcaggtaacg gtaagctacg    32820
tggacgctgt ggagggcaaa gaaaagccta ttacggtgca taacatggct gctcgtgacg    32880
```

```
tgcagggtag ggacgttcca gtggagatag acttccccgg aattaacacc cgctggctag   32940
cttctcgcgt agcttcccgt gagcttaacc aactgtcacg ccgcttagta aacggtgttc   33000
tgatctgcaa ccgcaaagcc tctaagcaca atatcggtga cgtggttctc gtggacctcc   33060
ctgaccgcga gttggataag cgtatcatgc gtgtcgtaga gaagagctac gggtcggagc   33120
ttaaggaaga gattcgcctt acggtgatcg aagataccgt taagactgtg gacccgttag   33180
taatcgacac tggcgactct gactggacaa gcccagatag tccaccacag cctgtcgatt   33240
atcagaagct agttgaggct acgtactggg aggtgtctac gttcatcggt gacacgccta   33300
tcgactggaa cacgctgggt gacagctacg ggtttatccg tgatttggca gtcagtgatg   33360
taggcttcgg atacgacatc tacgcaacca ccggaggggc tagtggcact tacacagatg   33420
ttgccgacgg tcagtttact aaccgagcgc agctggacgg cgctttgggt atgcctaccg   33480
gagcggactc tactgttaag atcaagggtg tgcaggacta tagcttagta atgctcaact   33540
cgcctgtcct aataggtggg gagctgtgct ggcttaagag tgtagacgta gcggcgagta   33600
cgattactgc gacacgcgt attgtagaca cggtgccaac aacacacagt gacggtactg   33660
aggtttggtt ctaccgagac acacgcacct cgttcgatga cactaagtac actatcggtc   33720
agacggtaca ccataagctg cttactaaga ctcctaatgg gattctccca gaaaaccaag   33780
cgtcggcaat aagctttacg atcaccggac gtgcccatag accttacccg ccagcacgac   33840
tacgcatcaa caacacgtac ctagggacgt cctctggtcg taacatgcgt atcgagtggg   33900
cacaccgaaa ccgcttaatg caatccgata aggtgcctat gccacaaacg tcgtcaagta   33960
tcgccgtaga gccggggact aagtacgagc tgaaagtggt gggggcttct agtggaaacg   34020
tagtccttga caagactggt atcgagggga ctctggagac gttggaccag aacgaccact   34080
tgtacaaact caaccgtgca gatagcagtg ttcggatcga gttgcagtcg agaagaccgc   34140
atggcaacac caccctgacg tcgtttacta aatggaacca caccgtagct tgggctgctc   34200
ctgagactga gactgtcacg ccagctggcg gcgctccgta cacactagga gaccgagtaa   34260
atgacattat gatgcagtat cgcgactcgt ttgtagagta caagtttgac atctcagcgg   34320
atagagccgc gaataatgct cttgagatcg aggtccgcaa gctaaacatg caggggggaga   34380 tgatccaagt agaagtattc cgtgacaata gccgtgtgca taacagcacg aagcaggttg   34440
gtagtatctg gcgtgtgagc tctcttgcag aaggagcata ccggatcaag ctgagtaaca   34500
ggtctactgt gacggatgtc aacatgctgg cgaggattgt accagcgtaa aactaatgct   34560
cacgtactag gcgcgtgagc cttttctgca actaattgag gtgatactat gaacgccgct   34620
gttaatagta agggtcggga tgacccgaac gtggttaaaa tgtgtccgaa agggcagggt   34680 acgaagggg acggcgatgt gccaaacgac accagtaagc acatagctgc ggtactcgtc   34740
ctgatagttg ccggggcgat cacatgggct ggcttccagc ttagtaataa caacgcagca   34800
cttatggctc aggcggcagt ctcgcaaagc cagaatgacc tttaaagca actaagttcc   34860 gatgtcagga tcatccagtc tggattagcg cagcaaaacg gggatctggg cgttctacga   34920
gcagacctca acaacacgat gagacgtgtt accggagtgg aggaccgaca gcagctcctc   34980
gacaagcagg tactacaagc tcttatcaat ggcaaacaag caaaggggta aaatcaatat   35040
gactaagatg cgcgagttta tcttgctcgc gctatccgtc gtgatagcgt tagccgtagt   35100
agtgggaatg gcagacccaa tggtattcgg tttactatta gtaaaaactg ccaaggcggt   35160
agtggcactg tcgcggttc gagtcgcagt ccactacttg gataaggtaa tcggagtcaa   35220
cttccgagag catgtgcggg ggtgggatgg tcaagcaatg gctatttaca tgggtgctcg   35280
```

```
ctttattggt gctgccgttc tcttcggctg catctttagt tagcaacact cagtacgaca   35340
agtacatcta caaggcatgg gaagagtacg taccagagac acaatgctgg ttatggctga   35400
aggcgcaata ctaccaagag agtttgctgg acccggaagc tactagccat gtgggagcga   35460
tgggattagc tcagatcatg ccgggaacgt ggatagatgt tagtaagaaa cttaagttca   35520
atccgagagc atcaccgtac gacccgaagc tctctatcga agccggagcg ttctacttac   35580
gctaccagtg gtcacagtgg agagccaagc ggacctttga ggatagaatc agtttagcct   35640
ttgccggata caacgctggc ttaggcaaca tactaaaagc acagcgcctg tcaggggggtc   35700 gggcagactg gaagtcgatt agttactttc taccggaggt cacggagag aacagcaaag   35760 agactatcca atacgttgag cgtatctttc gctggaaaaa gcaactggac gaacaccgaa   35820
gttgtgcagt ttactaaaat gataatgggg agcttcggct ccccttgttt ttactaagag   35880
ggaattacta aatgtttat tcgtttacta agcatgggcg gtacattact aaaaggacta   35940
tctgcgttct ggaaccgata caaattacta attgttatca ccctcgtcgc aggagctctc   36000
taccgcgcct attccatcgg atatgaccta gggtctacct acgagcgtaa caaggctgtg   36060
gtagccgttc tggaagccac aaccaaggct cgcacggagg agttccagta ctataagaag   36120
caactgcgac ttatgaccga aaaacacaac aaagagctaa cactggagag agaaaatgct   36180
cggatacaag caaccatcga caacaagcaa cttactaaac aaccagcctg caaaattagt   36240
aaagacgatg atgctaagcc tgttcttact aatgggtacg tcgagctgta caacgacgca   36300
gttcgagccg caaatcgagc cacccaagaa ggagataccg gaggaattac taaaacgatg   36360
cccaccgctg aaaacggtgg atagtaacga cccgtgggtt ttactaaaag tagccacgga   36420
gaatatagga acagcagcag tctgtatcct taactaccac accctacaag acactgtatc   36480
cgacagtggc gaaaaagaca gcaactaaaa actattgaca gccatgctac agttcgtgta   36540
gtatggcttc cgaaccatat ccaactggag ataacataat gcttataaaa cctgagacgc   36600
tatcagttcg cctagacgta acccgcgtcc tatcaccccg ctgcgctatc ctgctggcga   36660
taatacagca cacgtacgac catagctgtg cgtcccacaa tgactgccgg atgcacgaag   36720
gcaagcgttg ggtacgcatc agtaactctg agttccgaga gctaacaagc tttagtccaa   36780
ccacgattac taaagtatc caatccctag tgtcgttcag tatgatcgag actaagactc   36840
ttactaaaga taaaggcgat gtggctaact ggttcacagt cagcaaggag gagtagtcat   36900
gcgagccttc cgacttcccg atattctgca atcggacacc acgagcttta acacagacct   36960
agcggtaaag attgggataa cgcccgctat catattggga agtgttgctt actcgataga   37020
agctctctac gagagtggga ccgctaagga gtatgatggg agctactggg ctagggtatc   37080
cacacgcaag ctagccgagc gattcccgtt cctgtctacc cgcacgatag aacgcgccaa   37140
gaagcatctg gtagatttgg gattagtaag aattgacttt attggatctg agatgatgga   37200
tgttaaagtt gataacacat cgtggtggtc cataaacgaa gattctatta gtaaactgtc   37260
cagtttaggg gataccgaca aaatggcgga tacccctca gaccgacaaa atgacgtagt   37320
agggtctccg ccagaatgtc gggggatca ccgtcaaagt ggcggacaat ataagagtaa   37380 tataaagag agtaaagaat cttctaccga agattctacc ctatctaagc gtacgcgtag   37440
gactcgtaag cagagaacta aggactttgg gattagtaag gggaacttac cacagcgtag   37500
aaagagaact gcgaagaaag agactgagct tactaaacac actttcgttc ttgagaagct   37560
gggaggtgaa aagtacgttc ttactaaagc tggctttgat aagctacttg attttattaa   37620
```

```
acgccaagac atcccgctta gtgaagaaga gctcaacgca tggattgaac tcaacaagtc    37680
cagcttaggg ctgagaatca cctctaagac gcaggtagtc aagaccatcc agaattggct    37740
agctagattc aacgagagtg accgctggag gctcgataag cagttgggta agggtaacgc    37800
cccggctagt ggtcgaaacc gcccacagag gcttaacggt aatatcagcg acaagcacac    37860
ggaaagtgaa atacgcgtac caaaacactt acaaagatta gtaaataagg agtattagta    37920
aaatgaatga actaaacaag ttacgctcct tggcagaccg aattagtatt ggtcagttaa    37980
aggcgcgtcg aggggagttc ccagaaatcc tccgtaaact tgccgaggct ggggacgatg    38040
tatctgcgta catgaagcca cgattccacc cgcgtgtgaa caagatgcga actcgcggca    38100
tcccacagct gcacagacgt agcacgttca gctcgttcga agccaagggc agtcttgctg    38160
gcaagcgtga tatggtccgc gcttacgcag agaacttcac ggagatgttc gaggagggaa    38220
ccgacctcgt gcttatcggt ggtaacggga ccggaaagac acacctagcc agtgcgctcg    38280
gtctgacact tggggtgcgt acctgcatga ttgctgaagc cagatccttg tacaaggaac    38340
tcagtgagga cgaccaacga tacttcgatc tgttcggtga tgtaatcccg ccgttcaagt    38400
tcgtgaacat cgagcgcgtc atgcaagggc ttatgagcgc attcgatgcc aaggtcaatc    38460
actgggacaa cggtgaggag ttccgcgcca aggaggagga gttccagaac ttggtagagc    38520
tgaacggttt actaatcttg gatgagtatg ccgctaccaa agtcaacccg atgtgcttga    38580
acttccttaa ccgactggct acgtaccgat acgataatcg actaccgacg tgcgttatta    38640
ctaaccgaac ggaagaagag cttcgagagt acgactcaac ggcagcaagc aggttcttat    38700
ccagcgatgg tttagtaatt cgctttgacg agggagacta ccgtgcaaaa ggtcgataga    38760
cttcgacaag acttcaagcg tcttactaat caggagaaga atcaattcct gttctggctg    38820
gggctttctt cgcaggaagc ctcagaacgc ttttcagagc gtaagatata cgaatgcctt    38880
aagagctcac tctccaagct gtcagcagcc ggagatttgc aatttggggc ggttaaatcg    38940
ggtcagactg tgaacactt ccaaaaagta gttgagaagg tgaataccgc agctgaaacg    39000
ctccagccta atgagcgaga gcgtttctta gtaaaatact gcgctactgc tgttggtcgt    39060
ctggttgttc tggactcacc cttacaactt ccacatttac taagaatgat tgcccgtcat    39120
cacgagcaga tcatggggga cttaaaacgt gagctttctt actaagaata aacgagtact    39180
actcctcgtt gatgtatcga acataatgta taaggctatg cacatccata agaatcttac    39240
taaagatggt aagttcacgg gtggcattta cggttttatg gcgcaagtaa gcacggctat    39300
ccgtgagaac gaggctacgc atattgtgtt ctgttttgac cgcaagccgt acttccgtga    39360
agaagggctg agtattgact acaaagcagg tcgtgagaag tcgccagaga ctgaggaccg    39420
actagcccag actgaagacg ccgtacacga ccttactggt cacttcacta agtgggagtt    39480
cgatggtttg gaagccgacg acttgatcgc ctacgcagta aaacgctact accaccgatt    39540
cgacaagatc atagttcaga ccagcgacac cgacccttat caactgttcc gcgaagctga    39600
cactaagctg ggcttttgga agaaccagaa ggacggtcta tttacctacg ctgacttcat    39660
cgaaacatct gggttcacta tgggtgacga gtggttggca ttggacgcta tcactggcgg    39720
tcacaacgga tgggtaagg gcatcgtagg gtacggtcct aagaaagcca cggacctgat    39780
ccagaagcgt tcgagcaccg tacgcgactt gctctacatc tacccggatg cggggtacaa    39840
ctacacagtc atgcagctac cgcacgaagg aatccaccaa tacgacgggg aaatacgcct    39900
aggtcttaag agcatgtctc gtaaggacct tactaaattc tgtgcagcgt atggaattaa    39960
aatgcctccg gcatgggtag aaactttttac taaggttaaa taatggctaa gaacaagaac    40020
```

```
atgatgagta tcccggatgc tcaggacatc gtgacgctgg catgtttcga cgagaagtgt    40080
gctccgcaga tgttcgcctc ggtgacgctc aagcatttgc ctaacgacaa gctccgtgaa    40140
gtgttctcgc gtgcgaagga ctacttcgat gagtacggga tgcctatcgg ctctcaccta    40200
accaacgagt tcgctgacga gctgaatgac cgcaagcagc gtgcgcgtgc taatggctac    40260
cgagagctgt tagaaggttt gatggagaac tacgaggtag tcaacccaca gtacgttcta    40320
aaggggctga aggacttcct attcgtgcag gagatgcgcg gtaatattcc gaagctggtt    40380
gagcacttag aagacaacaa actggaagag gtagagaagg ttcttactaa actggcgtcc    40440
agtaagcagg aagaagactt caactacatc tgggcttcag acatggagca agtctaccac    40500
ggaatcttca accgtgaggt gggcgagagt cttgagatcg gcatcaagga actggatgag    40560
aacaacgtcc gacctaccaa gaaagagctg ttagtaatgc tggcacctcc taagcgtggt    40620
aaatcatggt tcggtgtgca gtgcttgcga gcaggcatcc agaacaagaa gaagaaatgg    40680
aagactttac taattacgct ggaaatggca cacgttaagt tcggtgagcg ttttgtgcag    40740
aacctatggg gtcgctgttt gggcgagcct cagacagtgt cgagcaccat cattcatacc    40800
gacgagtttg ggcacgtcca aaacattgac aatcagccgc gttatgagtg caagtctatt    40860
ctggacgagt tcgcagacga gaagcacgca gcgcgagaga ctgctcaatg gtttgagaag    40920
cactcgacag agcgtccatt cgtgttagcg cagttcccaa cgggttcttt tactatgcgt    40980
aaactgagag cgttcgtgga ctggcttgat aaggtagagg gatggcatcc agaccagatt    41040
atcctagact atccgggtat catgaagctg gacattaaca caagcgcca agctatgaac    41100 caactctatc aggacttacg tggctttggt gttagtaata acatcgctat ggtagcattc    41160
caccaatcga accgtgacgg tgcgcgtgag cagacagtgg acgacgtgat cgatgagact    41220
aacgcaggtg aagacttctc ggtaacacag cacgctgatt acttgatcac gtacaaccag    41280
tcgccggaag agcgtgagct taacttggca cgtttgttcg taccactaaa ccgtaacggt    41340
aaggacaagt accagatcgt tattagtcaa aactatgcca cgggacaatt ctgcttaacc    41400
agtggatacc gtgacagtcg ttataaggat atggtagttg aggattcgga cgaagctgga    41460
gaaaatccaa caagggagag ggcgggggtg gagccgcctg cgggataccaa aattgacgag    41520 tacgggaact ggttcgaccc agaaaccgga gagtcgtgga caggagcaag agtcgatgcc    41580
aacagttcgg gatttcttaa acagacgcct tgatgactgg cgctggttga aagcatagaa    41640
tgacgatacc gttatctaca atgaattagt aaacatgcct gtacgtccac agtttgagta    41700 cagacccttat atgtgtcaat tagtctgcca ctggatagga atctgccggg attccttcct    41760
cttcttcctg ccgttgtcgg caggtaagac caagttgata ctggacatat acaactaccg    41820
cctgcgtgaa gatgaggact tgcgcgggct tgttctcgtt ccgcgtgttg ctaacataaa    41880
gacgtggttg gatcaggtgg aggagcacac accgcatctg cacgctatcc ctattctggg    41940
tagcactgag gagaagcgtc gcgccctatt ctcagaagcg gacctgtaca ttgcctgtta    42000
cacagaccta cagttcttaa tggcagattt gcagcaagtg tcgggtaaga agaagcagaa    42060
gcgtaagcct aacgagagaa tgtgtcgtga ggttcagaag cgcataaaact tcgtggcttg    42120 tgatgagatc cacaaagcgg gcaaccacga gtctctgatc tacagactcc ttaagcgtct    42180
tactaagact gctcgctacc gctacggcat aaccgctacg ccgttcagtc gtaaggtgga    42240
aaggctgtgg gcgatcttca acttgataga ccacggcgag accttcggat caaccctaac    42300
tcagttccgt gaggtgtttt ttactaagaa gagaaacgta tggtccgggt tcttcgagca    42360
```

-continued

```
caagttcgat gacagtatga agagcgagct acaccgcttg atgcagaacc gctcaatacg    42420
ctacgagaac cacgaggtta aagaacttcc tccgaaggtt ccacgtgtag aagagttggc    42480
aatgagccct aaacagctgg agatgtaccg cgatgctcgt aagggtctag tcgattgtgg    42540
tagtggtgct aaggaagagt tagaagccgc gtacatacgc tcacgtcagg ctctttctgg    42600
ctacgtcgag tggaaggacg agaaccgtaa aacacaaggc atctacctcg atagcgacgc    42660
taagctggaa tggctgcaat ccttcttgga ggacacggaa gagaagtttg tgatcttcta    42720
caagtacacg agtagtgcta agcgcattac taagatgctc aagaaggaaa agtgcaagca    42780
ctcttggatc tggtccgggt gcaagaacgc agttaaatcc tacgatgact ccgcaaaaa     42840 ggacgacatc caaggcatgg tgatcaacct agcttctggg gacgctgggc tacagttcga    42900
aatggctcgg tactgcatct tctacgaatc accagaagac ccggtaacac gcgagcaggc    42960
ggaaggtcgt gtagcccgtg acggtccaac agccacagac agcacgtacg tcattgacct    43020
tgttactaag aagtcgtttg agggtaaatt actaaaatcg ctggaagaag gtatcaactt    43080
ccaagaggag gtactgtccg ggcgtataca ggactgggag gattagatgg taatgcttcg    43140
taagcgggtt gttcacgagc gtacgaaggg tggcaggctc cgggctaaga tagttcgtga    43200
gcctgttacg catagtaaac cgcaaccgcg aaaacgcaag aaacgaaacc taaggactc     43260 agaacacagc cagctctgct tgctagccaa gaagtggatt cttaagaacg ggtttggggt    43320
agctattgat gaccggatga aagcagcctg cgagactggg gagcagcccg acgctatggg    43380
gtggaatgct tccgttagta tagtgatcga ggttaaaaca tcccggtctg atttcctcgc    43440
agacaagaac aagaagttca gagcaaaccc aaggcttggt atgggagact ggagattcta    43500
tctgtgccca aaaggtctaa ttagtaaaga tgaggtcccc gaaggatggg ggctcctgta    43560
ctaccacgaa ggcaagatcc gccgggtgca tggcggtcct aaatccaacg ggtggtcgtt    43620
cgacggtatc ccctttgtag gcaacaaaga ctgcgagatg tcgtacatgt atagcgcact    43680
tagacgtatg gttgtgcgtg gacacttaga gtcgatgtac tcaatggatg gtattaagaa    43740
atgagtattt tcaaacgcag aggaacagat gcttggattg agatctttca caagcacagt    43800
atcacttacg cgacaaagca taagaactgt aagcgcggta acatagtaat agactgccct    43860
ttctgtgcaa actcagaagg caagttccac atgggtgtgg acaaacatgg tcgcttcggt    43920
tgctggaaga accaagagca ccgggggcac tcaccgcaca agctacttgt cgccttacta    43980
aaaatatctc cagccgaagc tacacgccta gtcggtgcag acgaaggtca ggtggacgag    44040
gacgagtgga actcgctgct acgaggtctt aagtcgtggg aggaagaaga aggcgtatgg    44100
gacgacgagg aagaggaaga agagccagct aaggtgatcg gtatgaagat gccaaagcag    44160
ttcatcccaa taaccccgaa cggtccggcg acagactact tctactactt gatggaccgt    44220
gggttcccac gcaaggacgt tcgcaaatta gtaaaacact tcaacctacg ctgctgtgat    44280
gtgtgggatc gtgttgctga caagatatgg tacgagcgca tcatcacacc cgtgtaccta    44340
gaaggtgagc ttatgtgttg gggtagtcgt actattaacc ctgacgacga gctgcgttat    44400
atgtcgctgc cagcggacga gagtgtgatc ccggttaaag agctggtata caactatgac    44460
aactgtatgg agggtggtaa gatactgctc ctagtagaag gtcaggtgga cgtatggaaa    44520
ctagacttct atggcaagca gcacgggata cgcgcagctg gtcttttag taagtctatt     44580 gttcctagtc aggtagattt agtaaatgag ctgaagaagc agtacgacca cacattccta    44640
ctgctcgatg cccacgagga agcttacggg ctctcattat gtgatttact aaacgggtac    44700
ggtaagcgcg ttaagaccat catgtgggat ggtaacgacg aagaccccgg agcggctact    44760
```

-continued

```
ttaaaagagc tagaaacttt ttttaaaaaa ttactaaaaa agactttact aaaacgaacg    44820
agggaagtac tattacctcg tcctcaacga agagggcaa gaaatgaatg aataccacgc     44880
gaaattagta aaatctgatt tccaaggcgt tcgagagatt tgcaaggttc cgcatccggg    44940
aattgcaggg cagttcttta cgtactttga ttttgacgat gagaacttgt tgggcgttcg    45000
cggaccgcag ggaccacaaa tcttcaaccc atctacttct cacactcaca tgggtgacgt    45060
gctgattaaa tggatggaaa caggtgacga agaagttttt actaaactta aacagttaga    45120
gcaaaaacct cgacgtcgaa aacgtttaaa agttgtcgaa gaagagtcaa aaacaactcg    45180
gaagcgacgt atagttaaga caggtgatga tgatgtcaat ccaaaccaac gtagaccacg    45240
cccaagaccg ccacacgaaa ccttccgagc agacttggaa gccagtattc cacggcgaaa    45300
tcgaagggta cgtaatgaac tgggttcgca acaaccactg gaaagtaaac cagcagcttc    45360
cagacgtcga agacgttaag caagaagcgt actgcatttt cctttacgtt gcggataaat    45420
acccgaacat tgataatcca cgttggttta tggatatgtt caagagaact ttcggttgtc    45480
gtatgattga ttgttctcgt aagcagattc gccacaaaga acacttcgcg gaaactgacg    45540
tattgtttag cgaaggagaa gaaagcctat ctcttactga aatgatggta ggcgatcttg    45600
aaacctcggc tattgctgaa aagctaatgg aagaggctga cggggaagtt aagcaagtgc    45660
ttcgtacact tctaaacatg ccagctgaag tctttactat ggttgaagaa gcatggacaa    45720
gtcgcggaaa gcgtaaggtt atgggcaatc aaatgctttg cgccttactt ggtaaagacc    45780
caaccaagac cgatctagtg aaaaagttg aagagcactt tatcggttaa ctaaaattgt     45840
tcgtatagac actgtacata cgaaattaac tcagttaaca ttactaaaga aggtaaagac    45900
tatgtcattg actaaagaaa tcctacaaga acttatcgaa gcgactaaca ccccacgtgc    45960
taagcgtgat tcgcacgaga agcacttgca gaaaatcatc aaggcagttg gcgctctgga    46020
cgacgaccag tgggacgctc tttcggacga agctgctgag tggtacaatg acgcggttaa    46080
cgcaatcaac gatggtcaag acattccggg ttctgataaa gacccaatgg aagagaccga    46140
agaaaaacca gcgcgttcac gccgtggacg taacacagaa actgacgaaa cggaaaacaa    46200
accaatgaaa aaagttctag tagcaatcgc acttgcagaa gtagttaaag gcatcacagt    46260
aacagtagtt tgcggtgacg atactttga aggcgaagta atcgacgtta ctaaaaaagg     46320
tcgcggcaaa gcagctaaag ttgaagagtt cactctgaag actgcggacg gcgaagaagt    46380
gttcggcgct gaagacctaa tcttcgacga aggtgacaag atcgaacgtc acgacgaagt    46440
agctgaagaa gagaaaaagc ctgctcgttc tcgtcgcggt gctaagaaag acgagccaga    46500
agctgaagaa aaaccagctg gtcgcggttc tcgtcgcggt gctaagaaag aagagccgaa    46560
agcggagcca gtagaagttg aaaccgagat cgcgttcaac gacatcgcta aagacgacaa    46620
gctgaagctt caagtcgaag acgacgcttt cgaaggcact gttaaagcgg ttaagaaaac    46680
tggtcgcggc aagaacgcta aagtagctga gttcactttta gtaacagcag acggcgaaga    46740
agttttcgaa gcggaccaca ttgtggttga agaaggcgac aagatcatcc gtatcactat    46800
ggaagagcaa gcgccagcta aagaagaaaa agcagcaggt ggtcgtcgtg gtcgcggtgc    46860
taaatctggt agcgcacctt cagcagctca ccaagttcgc cagcttatct gtgagaacct    46920
agactcagac aagaaagcga ttgaagagct aatggctgaa aaaggcatcg acatgaaacc    46980
gtcaacgttc gatgtacttt acagcgaagc gcacagccta gtagcagtaa tgcgtgaact    47040
agacatgcta gcgtaattcg gtacagtgta gccggatgga gattggggag cttcggctcc    47100
```

```
cctttttcgt attagtaaga cgaggtttag taaaatggaa caagagaaat tcatagacct    47160
tccagagctg cgtatgctgg caaagtcgaa agcacaacac acgctacaca gaggtttaac    47220
tttagtaaac cataaagggc atacagccca cgtattcggg ttcactacgc tggacctact    47280
agcagcttca atcttcgcac aagaagccaa cctgctctta gcatcccagc catacaggac    47340
taccaacgac catatcctgt tctttacacc aacaagccgc ctagatctcg cggacataat    47400
cgttgggttc aagtacgacg acaacaataa ccccagcaac gtccgacagc agtattcggt    47460
cctcaatatg gatgtttgcc cgacaatggt ccagctgaca cctccgggaa cagactggaa    47520
gccttgctgg aatagggct tgcactacgg accaagactt agtatagtta cttccggcaa    47580
tgttaatctc atccgttgga tcttgtaacg tcttggcttg ttacactagg gaggctatta    47640
tagtctccct ttcttttgtc tgccgtatag gttcggacaa ccaaccaagg agaataacat    47700
ggctacacta gagaaagccc aactacagcg cgtattgaac ttcatcaagc ctgcgctatc    47760
ccctcatgat ttcgttccgg tactatcaca cttctgtttt acggaagaag gtgacgtgta    47820
cgcttacaac gacctagtag gcgttactgt acgcgagcac gacttcggga tcgtgggtgc    47880
tcttcccggt aaggatttac taaaagtaat aggctccttc ggcaaggctg aagttagtat    47940
cgcagagatt gacgacggtg ctggggtgct tattaaatct gggcgttcaa agactaaatt    48000
agtaatgcta ccggacgatg acttcgttta cgagcccgtt actaacacag accagaaacc    48060
tcgtgtagag tttgaactgg acgaagagtt cttaactgca ttcaagaagt gtatctctgg    48120
tataggtgat gaccctacca gccctgcaca gatgggtatc acgatcacgg atagtttcct    48180
gttctctaca gacaacgtca caatcaccgc gtacagcctt ccagacccaa ttgaggggat    48240
tggtcaagtg atactgccaa aaccgttctg tgagcttgtg gtagagcttt ctaagtacaa    48300
taagtcggag attatcacca tgtcgttcta cgacgacaac gtgacggcta ttctggagga    48360
tgagtcggta gaaattacta cacgaatcct agaagatgac gagccattcg actttgaggc    48420
agtactcgac ccgttcctag aagataccga cgctttagta aaaataccga acgagtttaa    48480
agacatgttc gcacgcgctg aagcggtcct aggaaaaggc gacgaagcca tactagacat    48540
cgcagtagaa ggggacgttc tgtttatctc ggctaagtcc ggtaagatgg agctcgacga    48600
tgagtgcgac tttgactccg acgacgttaa gttctacgca gatgcaggca tgattgcccg    48660
tgcttgccaa tttacaacac acgcagccct gctcccagca gcaatgttct tcagcgacgt    48720
aggggcgttc taccacctaa tcagccactg tgaggaataa cgatgggatt ctttcatact    48780
aagggagcca aaggaggctc ccgacgttta actggtaagc agcaggcatt cgagcagcag    48840
aagcatttac taaaatcagt gggtgctaag aagttcgaag gcgtaggcgt gcagcctgcc    48900
gggtctgata atccgtttgt gtacatccta gggcttacac caacacctaa ccaactcgcg    48960
agaaacgacc ttactaaagg tgagaccgcg caggttatgc gtaagtactt tggtcgtgac    49020
ttctactaca acgactgccg tcacggagct gtagtcgcg agacgtttgc tgagctggac    49080
gaagtgatcg acgacgtggt gatagagcaa tggcgtggta ttaccgagca ggacatcgaa    49140
gagactaagc cagcggtagt tgtcgctctg ggtgctggag ctttacgctt cttcactggc    49200
agtgctgaca tccacggtat gcacggcaga atgctacccc acaaagtggg taatcacacg    49260
ttctggctac tcccggtgtt tgacccacgt tgggttatta gtaaagacca cgacttcttc    49320
gtgaacgagt acgagatctg cgttaagacg caggtcagtc gcttgatgga cctgatcgaa    49380
accgggagcc tgccggagcc tgttgtttac gacagtaact acgacgatgg tatcgagatc    49440
atcatgggtg agggcgtggc agatgtacat cgcgtagaag atgtactgca tgacatgctc    49500
```

```
aaagagccgt tggtatcggt ggactacgag acgcaaaacc tgcgcccgta cctagaagac   49560
tcacgcttac taactaccgc cgtgggaacg tttgaccgta ccgtggcgtt cccggtagac   49620
caccctaggg cttggaacaa taagactcgc cgtcaggtgg tcggtctgtg gggtgagtac   49680
ttgtgtcagg ctcctcgcgc tatcgtttac aacgctacga tggagcaaga gtggacagcg   49740
cactactacg gttttagtaa tctgcgtaaa acccagtggg aagacctaat ggcagcagcc   49800
tactgtctgg actcacgtaa gggcattta tcgttagatg acttcatcaa gtacaactgt   49860
ggcttcgacc tcaagaagct gtcaggcaag atgaataaag ctaacatggt gaatgagaaa   49920
cttgaccgcg tgcttatgta caacggacga gacgtgaagt ggaccttcaa gggattcgag   49980
attgcccagc agcgtttaga gctggaggga gaagaacgtc cttaccatac taaggttcgt   50040
aactctgccg ctctgaccgg gatgcaaatg cgtggtatgc cccgtaacga ggagggcttg   50100
attgaactac gagacatcct tactaaagac atcgcggata ccgagcagga gctgatcaag   50160
acgccggagg ttcgtaagtt cgagcgcatg aacgatatgg actttaaccc gtcgtcacca   50220
gagcataacg tcacgctatt ccgcgacatc ctcaagcgca aggagggtaa gaaggaaggt   50280
aaggacaaga agggcaacca gaagtacagt accgacgaag cggcgcttag tgccatgccc   50340
gccgatgagt gtccttcagc gcctcttatt cttaaactac gtggttttac taaacttaaa   50400
tcgacgtatg ttgacggtct tctaactccg atcacagagt tcatcgggga cgagaagaag   50460
cgtaagggtc tggtgtaccc ggatgggtta ctccacccga actacaacgg gatgtttacc   50520
gccacgggtc gcttatcttc ggacgagccg aatgcacaga acttccctaa gcgtaagaac   50580
cgacacatcc gtaagccgat agcaccgcct ccgggcttcc gggtagtctc actcgacttt   50640
ggtcagattg aggcgcgtgt attcggtatg gcttcacgag accctaactt ctgtaacgca   50700
ctgtggaaca acctagatgt tcactttgac tgggctgtta aaattagtaa cgagtatccg   50760
gggattctgg atcgaatcta cgacgagtac tacgacaaga tcatcaagat ggtcgatggt   50820
ggtaaatcag agtacgactc gatcattaag tgtcttcgtg gtgacgttaa gaaccagtgg   50880
gtgttcccgc agttcttcgg agcaggcttc aagtcttgtg ctcagagcct acacatcccg   50940
gacgagaacg cagaaaacct acgcgctatg ttctgggaag agtttgctgg ggtgcaggag   51000
tggcagaatg aaacgctgga gcgtgcttac cgagacgggt acgtgagaac tctaaacggg   51060
tttaagcgtt ccttccctat gagtaagcag gagatcatca acacaccgat acaaggcacc   51120
gcagccgaag tagtactgga gggtctgtgc ttactaagtg aggaatccgc tctactggaa   51180
gacgtgtaca tgcaccctat catgcagata cacgatgacc tgacgttcat catgccggag   51240
gatggtatgg acgagcgtat aatgcacgta gcggagatca tgactggtgt gtacaagacg   51300
tttgactttg taaacgtccc attgcttatc gaagccgagg aaggacctaa ctggtgtgat   51360
caaaaggttt acgtgagta ctcatctacc cagttcgggc atatccgcgc tgactaatca   51420
aagcctccct agggaggcta ttttactaat agtaacgagg taacaatgaa acagtatcta   51480
gcacttgctg agcgtatcgt ctctgagggc gagtggatcg agaatgagcg cacgggcaaa   51540
aagtgcctta ccgtgatcaa cgcggactta gagtacgatg tgggagcaaa ccagttccca   51600
ttagtaacaa ctagaaagag cttctggaaa gctgcggtag ctgaactgct gggatacatc   51660
cgtggctaca gcagtgctgc tgacttccgc aaactgggga ccaagacttg ggatgctaat   51720
gccaatctaa acgaggcgtg gctaagtaac ccacaccgcg aaggctacga cgatatgggt   51780
cgtgtgtacg gtgtgcaggg tcgtgcttgg acaggctcgg acggcactgt ggtagaccaa   51840
```

```
ctccgcaaga tcgtagacga tattactaag ggtgtggatg accgtgggga gatccttaac    51900
ttctacaatc cgggagagtt ccacctagga tgcctacgac cttgcatgta tagccaccac    51960
ttctcgctac tgggagacac gctttactta aacagcactc agcggagctg tgacgtaccc    52020
ttgggtctta acttcaatat ggtgcaggtc tacgtgttcc tagcaattat ggctcagatt    52080
actgggaaga aggcaggtaa ggcttaccac aagattgtta acgctcatgt ctacgaagac    52140
caactagaac tcatgcgcga cgtacagtta aagcgtgaac cactaccgct acctacgctt    52200
tggattaacc cagacataaa gacgctggaa gacctagaga cttgggtaac agtggacgac    52260
ttccgtgtgg acgactaccg tcaccacgac ccaatcaaat atccattctc agtttagtaa    52320
ggagaacagc aatggaaaca agaccactac acgtatcact acgtccacag acctttggcg    52380
agatcatcgg tcacgacgct gtagtaaaag acgtgcagaa tcagctcgat aacaacaacc    52440
aacgctgcta cctattcatg ggtcccgcag gctgtggtaa gactactttt ggtaatgtca    52500
tcgcacgtca cgtagagtct aagaacatca tcgaagtaga cgcgggtagt accagcaaag    52560
cagagcagat ccgtgagctg gtagataagg ctaagtaccg tgggtttggt gaaaacccta    52620
tccgcgtcta catcttgaac gaagtgcagg ctcttagtaa ggctgcttgg gatgccatgt    52680
tggacatcat ggagaaccca cctcaacacg tgtacttcat cctgaccact acggaatccc    52740
cgaaggtgcc taaagctgta aagactcgct gcgcatcgta cgagcttaag ccgcttagta    52800
agaaggctat taatgatctc atcgacatgg tcatggacga agccgatatg gacatcccgg    52860
acgagttcct agacgtggtg gctgacaagt gtgaaggctc tccacgccag tgtatccaga    52920
tgctgcttaa ggcagagtcc gctaagaacc gatctgagct gaatacgtta cttgatgaag    52980
ccgagagcga caaccagatt atagaccttg cccgaacact cgctttttact aaaggtaaaa    53040 aatggggtaa agtgcagacg atcttgaagg acctcaagga cacaccaccg gagagcatcc    53100
gtattgtagt aactacgtac attgctgggt gtatgctcaa tgcgaagaca gaagcagacg    53160
cagagcgact acaccacatc ttggatgcct tctctacacc atgtaaccct accgacaagc    53220
tagcaccgat cttactagca tgtggtgaca tctgcttcgg ggagtagtaa atggcatacg    53280
atgtaggtga gcaagctatc cgctcgttta agaaccgtct acgtatagat aagaacgatt    53340
tggacaacga gctggtagag caatcacacc tcttcttcga agtatctgag cgccttactt    53400
gggctaaagc agaacgtgat gaagttaagc gcgagtgtga tgagctagcc ggggaactta    53460
aagcggacct attcgcagaa aaccctaagc tcgctgacac taaagctaca gctatcgtga    53520
aaaaagatcc tgactatcag gaacgttacc gcgaaaaatc tgacgcggac cgtatagttg    53580
gagcatggga ggcattagtc gaagcgttta atcacgcgg ctacatgctt agacaattag    53640
cagacctcta tgtggctaac tactactctc caattagtgg tggtgagtct caggacgata    53700
agcgtcgcaa gcgtgcggaa cgtgatgacc gcagcaaccg acgtagaacg cggagaactt    53760
aacatgggtg ataaatttgca gctggcagca gcaattatgg tattattccc gattggagcg    53820
tatgtattag ctcgcatggc aacaaaggct tacttttta gcaagctaga atttcttact    53880
aaagttaaac agaaaggatg gtaaacatgt cacgacgtaa tcgtaacagc ggcggtcgta    53940
aaggcttcga gtacaagaag cgttctaaag aacaggtgca gaagcgtgcc gaacagcagt    54000
caggcgactt taagtcaatc ttcaaagaag gcatcaagat gtacaagcct aagaagggtg    54060
acaacgcaat ccgcatcctt ccggctactt gggaagaccc ggatcactac gcactagatg    54120
tacacatcca ctacgtgtt ggtgctgacg aagagcgtgt actagcactt cacgagatgc    54180
ttggtgaaga cgacccaatc cgtgagatgc gcatggagta cgaagccgac ggcaataaag    54240
```

```
aaatggctaa ggcttgccgt ccgggtcgcg cttgcgcaat gtggatcgtc gatatggaca   54300
acgaggcgga aggtcctcag atgtacctag caccaccaac ggttgacgct ggtatcgctc   54360
aggtgagtat cgacaaacgc tccggtgaga tgttcgacat tgacgaccct gagaacggat   54420
acgaagtcta ctttactaaa cagggcgaag gtatgaatac caagtacgta ggcttccagc   54480
ttgcacgtac tccgtctgaa gtagatgaag agcacttaga ttacgcaatc gacaacccga   54540
tcccggactg cctagtttac ctagagtacg aagagattga gaagatgatt gcaggttgga   54600
ctccaacacc tcgtggcaag ggtggtaaag atgacaaggg caaagaaaag cagaagtcat   54660
accgtgggcg agatcgtgac cgcaatgatg gtgacgacga tgatcgtgat tctaagtctg   54720
ggggtgatcg cggtgatagc gattacaact atgatgatgt acttaaagcg gattgggatg   54780
agcttgaaga catcattgac cttgaagagc tggacatcga cccgaacgac ttcgacgaag   54840
acgacacgga aggctgtgct aaagcaatcc ttgaagagct gggcattgag aaacctaagc   54900
ctactcgctc ttctcgcggc gggcgtggta gtcgccgtgg tggtgatagt gatgatggtg   54960
attctcgatc ttcccgccgt cgtggtcgtg gcggtgacga tgatgaccgt agcgaacgtg   55020
ttcgcggtat gcgtcgaaat cgttaagaag tatccacggg atatagttta gtaaaccaag   55080
ggggcatatt catgtcccct ttattcagtt aaggagatta gtaaaatgag ccgaggtatt   55140
attgtagcgg tagaaggctt cgacggttct ggcaaatcca ctttagtaaa gctgctggta   55200
gaagagttag ccaactacga agtgaaggtg gttcaaacac gccaacccgg aggaacgcct   55260
tacgcagaga agatccgcga cctgctgatg tctggggacc gtgaccgcag tcaagccgta   55320
gaagcacact tgttcttagc cgcccgccaa gacctatgcg ataagctggt agcgcctgcg   55380
gtagaagagg gggctatcgt agtgtgtgac cgccattacc tatcgtccct tgcaaatcaa   55440
ccacagtgcc gatctctgtt cttagaaaac cgagtgtttg acccggacgt ttggatcatg   55500
gctcgatgtc cgttcccggt ttgcatccaa cgcagtgagc agcgtggtga cgacgatgcg   55560
tttagtaacg atgagctccg agagaagcgt gcccagtatg accgctacca gcatggtatc   55620
aaagacattc taccgttcac ggcgggggac tcactgttca cggtggacac cgacttaggt   55680
attacaagtg cgcgtgagca gatcaagaaa gtagccagct acttagtaag cttaaataaa   55740
caactcccgt ataattcata gtgttccact cactttaagg ttagtaaaat ggcagagaca   55800
agacgtagac gtactaaggc agctgagaaa gaagaggctc ctaagtcacg ttcacgccgt   55860
acacgttcca cggaggctga gaagcctaaa gaacgtgcta cgcctactt tgtatcgaca   55920 gagaagggag tagaaggctt cagtaccggg tgttgtctgt ttgaccaagc cctaggtggt   55980
attggttggg ctaccaagcg tatcatcaac atagtaggcg ataagtccac aggtaagacc   56040
ctcctcgcta tcgaggggat gatcaacttc caccgcacgt tcatcgacca aaacccacgc   56100
attatttaca aagagtgtga gtctgcgttc gatgagccat acgcagaagc tctgggctta   56160
ccactcgacg acattgaggt agacgacgac cttgataccg tagaagacat gtacgaagac   56220
attgagcgta tcgtacaaga agcagagcgg gacccacgcc ctatcttgta catcgtggac   56280
agcttagatg gtcttagtga tagagccgag cagggtcgta agattgacga agccagctac   56340
gggcaggata aagccaagaa attatcagag ttcttccgca agaagaaaaa ggtaatggct   56400
aaggctaaca ttactttact aattatcagc cagatccgtg ataatatcaa cgcggctgcg   56460
ttcggtaaga agtctaaacg ctccggtggt aaggctttgg acttttactg tagtcaagtt   56520
gtgtggctag ccaacttagg taaagttact aaagctgtta agggcaagaa gcgtatcgtt   56580
```

-continued

```
ggtgttgaca tccgtgcagc cattgagaag aacaaggtgg gcaacccgtt ccgcacagct    56640
gactacccga taattttttgg ttatggggtg gatgacatct acgcctctgt agagtggcta    56700
cagtcgaacg tagggtggga tgttcttgag gacctaggat tcaagaagac aacctacaag    56760
gctatgtgcg ctaagatccg tgacaagggt ggtcccgaag ccaaggagat gcgcgaatct    56820
cttaataagt tagtaatcca ccactggcag gacatcgagc tagacttgat gcctaagact    56880
ggtaagtatt agtaaaggag gcagtatgcc tgtaatccaa gcaaccagaa aacccactac    56940
gctatcctgc attcgttggg agggtgataa cctacgtgaa gtacttgagt tcaccgggaa    57000
gcactttaag tttgacaagt ggttcgccag cttcgaggag tacgaagccc atgtacgatc    57060
tgagggtaac atcttcaagg tattcacccg aaacggcgtt actgaagcag ccgtaggtga    57120
ttacattatc cgtggggtag agggtgagca ctatccatgc aaaccagaca tctttgacga    57180
gatctacgat accagtggtc gtgtgtttgt acctatggca gacgctagca cgcaggagtt    57240
agcggcgcgt ctggaaaaat gcaagggta cgaaccctac atgcttaact ggatctgcgt    57300
gtcgtacaaa gagtgtggta tttcccgcat cccagtctac gagtgctacc acccggacca    57360
caccgtgttc tacgcaagct cagagttgca gcaggcagta gacgcattta gtaactaccc    57420
ctacctaggg tagcgtatcg taactagggg gcttcggtcc ccttcttcaa ttggagacca    57480
atatgatcaa cgaagacctg tacatggggc tagactgctc cctcaacaac tcaggcatag    57540
tggtctttgg taaaactact ggatacccttt atgaaagcat taagccgaag tgtaagggat    57600
atgagcgcct tgcttatatc cacgatagtc ttactaaaat actcgctaaa tacccaaaca    57660
tcaaaggcgc taacatcgag cggtatgcct acaacaaagg tggtagtgac aagtccaacg    57720
ccgggatggt atttaacatc ggtgaaggcg gtggagtcgt gcgactggcg ttattttcgg    57780
ctggcatacc tgtcctgctc actagcccaa acactgggaa gaagtacgca actggaaagg    57840 gtgttgggg caaggagata attctcaagg aagtgtacaa acgcttcggt gaagacctcg    57900
acgacgacaa cttagccgat gctttggtaa tggctcgtat agcttaccac tggttcacag    57960
acgactacga aggacttact aaggctcaga tagaagcggt taaagcagcc tctcttgagc    58020
atgagccccc taagcctact agccgtcgta acggagagt aaaacgcaaa tgaatcgttt    58080
gattgctgcg gatacccact tcacacccaa gcccctagac gagtaccgtt ggggcttttt    58140
tggctatctg aaggactggg ctatcaagta cgacgttgac gagatctgga tactgggaga    58200
ccttaccgat gctaaggaag gtcactccgc tgagttcgtc aatagattag taaaccacat    58260
caccgagcta tcgaggtag ccccggtgtt tattttaaga ggaaatcacg actatgctag    58320
ggaacatgtc gccttctttg agtttttacg taagctgcct aatgtgtatt ggattgaccg    58380
ccctactact gtctatggcg tccgtgcttt tccacatagc aagaaccctg cggaagattg    58440
ggcaacacta ctcgacgatc tggacgagta tgagtacgcg tttttccacc aatgtttcgt    58500
gggttcgcgc tcaagtatgg ggcatatcct cgacggaacg gacttagacc ttactaaact    58560
taaaaagtgt aaggtgtacg ccggggacat ccacctacct caaaccgtcc gtgggattga    58620
gtatgtggga agtccctacc cgacgacgta cggggaccgc ttcctaggac gctgcttact    58680
agagacaccg gaagggcgta cccagttgca ctacccacg atccagaaat gcacgttagt    58740
ggtagagtca gtctcggaaa tttatgacgc ccacgtgtat ccgggagacc aagtcaagat    58800
ccgctacaag attagtaaaa aggaccgggc ggagtggaca acatcaaaaa acgccataaa    58860
agctgcctgc gatgacttgg gagtggtgct gggtggaacg gagcttgtca cagacgtggt    58920
cgaaaaggct gagttgaagg attccaccac taaggtgact aaaacctctg agaaagccat    58980
```

```
tctgacgcaa ttcgcccata aggaagattt gccagatgac taccttgacg tagcccttac   59040
tattctgaag gaggagtgat ggactttata ggcattcgtg gggagaagtt taagagcttc   59100
gtggaaccct tcgacttcac cttaagcaaa ccgccgggac tgtacttact aaaaggcgag   59160
aacgtagccg agccaagcct aggtggtaat ggtgtgggta agtccaccat ctgggatgct   59220
ctgttctggt gcttaaccgg gactactctg cgtaagctga agaacaccga cgttaaaccg   59280
tggggaactt ccggcagtac atgggtggag gtaatgatcg cactagatga agatttacta   59340
acagtgcgcc gacaaactaa ccctaacgcc ctaacgttag agtctgatat gcaccagaca   59400
ggaccgcagg acatctcgac agaggaacta ctccagttct ttaacgtgga cgagacccag   59460
ctactccact ctctgatcgt agggcagttt gggacgttct tcttcgatat gctcccagcc   59520
aagaagcagg agctattctc ctcgatacta tcgctggacg tgtggctcac ccgtagtaag   59580
acagccgcac aaatggtgaa ggttcttaag attggactac aagaagcgga gcttgagtac   59640
gggcgattgg agtcttcact tgagctgctt cgagctgtag cctacgacgg ggactctgaa   59700
gattgggaga acgacacgc cgaggactta gcagagtgtc aggatagaat agacggtatt   59760
actaaagagc tagaaggtat cgacgtgtca gccctagagt ctgaccggga ctggacggag   59820
cagctgctga acgatactga ggctacgatg cgtgagctgg taaaagagat cgacactatc   59880
aaagaagaca tccgggaagt tgagaacgat aagcgcgatg cagacaacgc tatcgacgac   59940
ttactagaag acttcgagga tactcttagt aagggcgctt gtaattactg tggtcacgaa   60000
gtatctgacc gggagctgga tcgcttagag gcttcaacta aggttaaggt ggatggttta   60060
gaggacaaga tagacgagta caacgacgag ctggctgacc ttaaatccga cctagcgcct   60120
aagaaggagt acctagagga ccggaggagt gaagccgctg gtttgagcga caagcttagt   60180
aagctggatt ctgacatcag aatggctctc aaggaccgta agagtttatc ccgcgacctt   60240
agccgtgcag aagacgtcta caagaagtta gagcgagaga ctaacccttg gctaagctg    60300 cgtgactcga acgagtccga tgctattgag atgggtgcga agctggtaga cgctaacgag   60360
acgattagta atctgaacac ggctattgag cgtaccaact actggatcaa gggctttaaa   60420
gacgtacggc tctttatgat cgacaactac ctagtagacc tagaggtgga ggttaacaac   60480
tccattaagc agctaggttt agacggctgg cgtatagagt tctctgtaga ccgtgaaacg   60540
cagcgtggta cggtcaagaa gggcttcgag gtttacgtgt actctcctcg aaatactaag   60600
cctgttaagt gggagtgttg gtccggtggg gagtcctccc gtcttaagct ggcaggtgag   60660
ctggggctta tggagatgat cttcacggct accgggcagg agcctaatat cgaggtgttt   60720
gacgagccca ctagctttat gtcccaagag ggtatcgagg acctgctgga actactaagg   60780
gaccgtgcct tactaaaaca aaagtgcatt tacatcatcg accaccactc agtcagcttc   60840
ggcggctttg agggagtcat taccattcaa cgcgacaact taggaagtcg catactggag   60900
aagtaacatg attcatttta ctgttagtaa aaacgcaaca ctagcccacg cttgggttcg   60960
caacgtcctg tccgcagagg gacagattcc attcagcact atgatgcttg atgtggagtt   61020
cagcttccat gccgagtcgc tatcagactc cgacgatgta gccccgcacg agtacctaac   61080
tgtgtacgct gggcaagtgc tggaactgtt tgacggcgta cacatcctgt gggacaagga   61140
cgagcgtgct caagtggtaa cagctgaaat tcacgagtac tacggtgggg tgcggtcact   61200
aagtacaccc tacaacccaa cacttgagca cgtgtccggt atgatctacg cggtaatgca   61260
ccgcatcctc tgtgcgagta actttactaa ctcagaagac ccggagctgg agcttgtttg   61320
```

```
cgtaaaagtg tcggaccgag ttactaacac taccgtgacc tatgattccc tagcattcga   61380
agggcgctta gccctaaacg ctaccacctt ccgctggagc tcttcagtac tggaaacagc   61440
cgcgcttgat gtggtatctc tgttttctga ggacgtccgt atagatgttc cagtggcaga   61500
gaaaacggta gacaagtatg agtaacacgg aattaggaat cggtgatacc gtggaggtga   61560
ttgtcactgc caatcacttc ctagagaaat tttgtagagt gggtcgtatt actaagaagc   61620
atggctcatt ctactgggta aagttcaagt ttaactttag taacgacaat aagcatttgc   61680
actgttacga ccagattgac ttcggaccat ttagcatcaa ccaattaaaa ctgttggaga   61740
aaaataccaa tgacacaagc agcgaagaaa gtactaagcc taacgacat  catcggaaag   61800
ttcgcaggca gcgtaatcga gttgaaccag aacaaatttc ccgcaaacct agagagcgtc   61860
gtgcaagact tagcacacca cttttaagttc ttctcacaaa acctaggcgg cgtagatatg   61920
gtggactaca gccgtggtga gttttacgac ttactacacg agtacatcat ggcagacgtc   61980
cgctgtgaag agtggaatcg ccccgacggt gaagggcact ttatcgacct agttgcgctt   62040
gtgcagaacg tgacttacgc cctctatggt ccgctaagcg ttgtccatga agtaccacca   62100
gagaatgatt actcacgctt ggattcattc gatagtaaga agcaggtgcg tgcagcggtg   62160
atcgcatcgt actcgattga agactgtgaa gtgactgtcc acgtggaagg cgacgaccag   62220
tacccactag agacaatcaa agtaacccac gacttcttcg cccgtgctgt accagtggcg   62280
gaccagtcag ttttagtaat ctacgagaac ggctatcagt cgcacagccc actcgatgta   62340
ttcaaagctg gtcacgtacg ttcattcgct atcaaagacc cggcgtctac aatgcctccg   62400
gcagcgtaca tggacagctg tgagatgacg ctatcggaac agtactttga gcctgacgct   62460
acgatcatta actgcatgaa agagttcatc attagtggta acgttctgga tgggttcaag   62520
aagtctatct actacggcaa agaagccccg gtagttgact tgatggaaaa gctagagcta   62580
acagacatcg cagactggcg agcactaaac ccacacgaac agaagatcct acatgccgtt   62640
ctgggtatgg ctacgagag  caccgagtta gtcgaacaaa tctacggcta catgttccaa   62700
ggtaaggagc tggaccttaa gaacttgtac gaagaagtag gcgacaactt attctacgta   62760
agcactatgc tcaagtgcct aggtgtttct tacgagcagg caatgtacga caaccacatg   62820
aaacgcatga agcgttacgc gggtggtaag ttctccccag aagcggcaat caaccgcgat   62880
gtggaagcgg agttgcaaca gcttactaag agtggtaatc tagctgggca gtaaagtaaa   62940
tcagcttcca taactctatg taggttccgg gcttggacca catgtttgag gtctccgaaa   63000
ggggacctct tttttatct  gtagaatgta ggtatcctat ccccggtaaa tagcacttta   63060
gttgacgggg agccctatgt cagaacaagc agaagagaag ccacgcagac gtcgccagcg   63120
caagcagata ttgagcgttg cccagcgtcg tctccagcgc acgtggaagc tggatgaaga   63180
gacgaaagag aaattcatcg aagcgatcct aaaaggcatg agcgaagagc gtgcctgtat   63240
gttagtaaga atcaacaagc tacactactt cgagaagaag aagaaagtac acgagtactt   63300
gaactcaggt attgagccta caggtgggga cgacccacgt agtaatatcg acgagtgggc   63360
tatgttcatt gaagaggtcg aggcggcagt agccgagcat gagctaaacc taatcgacga   63420
cgccttagac attgattctg agtcgaagaa caagaactac tggcgcgcta acatgacaat   63480
ccttgaacgt cgtaaccgta cagactgggg tcgtcaggaa tctatcacac acagcatcgg   63540
gcactacgac ccggatgaca gattcctta  atcttagtaa acaacctagg gagcttcggc   63600
tcccttttct tttgggcgtc gtataggtga tcgtcaccaa caaagcctag gaggaatggc   63660
atagtgaaag aacgttaccg tgacgagctc acgtggtggg agaagcgcct aggtgtttgg   63720
```

```
cgagttaaca aggactcata cgacacaact tggggctact tcgcaccgcg ctgggctctg   63780
gagttcaagg tcaatgcagg cgggtacttt agtaaccagt gctcgctaga cgtgggsttc   63840
atctggggac tgtttcacat taagctgccg atacgtctta agaaccacga ggagagctgc   63900
gagtggaaca actacggctt tatgtggtac gagaaccaat gggtattcaa atggggcgag   63960
aagtctaagt ggtgggatgt tccatttatc tcatggacct ttgacttcca tcatgtaatg   64020
cacaaagacg ggcattggtt aaacggcgac caagcgtgga agaacgagga gattgaaaaa   64080
gaaatctttg attacacgta tgtattagag tccggggaag ttcagcaccg caaggcaact   64140
tgctaccgtg agcgacgcca gtggcaccgt aagtggcttc cgttcctaaa gcgtacagtt   64200
acttcgatta gtatcgagtt tgatgacgag gtgggagagc gtagcggtac ttggaaaggc   64260
ggtactatgg gatgcggttg ggacctactg cctaacgaga caatcgagca gtgcttacgc   64320
cgtatggaaa agaacgcaa gttcacctaa acaactttt aaccacgtat aattaacagc   64380
aaccgggaat aatcccttaa ctttagtaaa aggaaactc taatgagtaa gaaactatta   64440
gtaccagcat ttgcaactgc gcttgtagca ttcaaagacg aattactaca gcgtgcagct   64500
gaagtgaagc agaaagcggg tgaaatggct tttgacatcc taacaggtgg ttcaactacc   64560
gtagacactg agaaggcaat ctcgaatgct cagggcgctg tgggtgccta cgagtttgca   64620
cacgaagcgg tacaagcctt actacaacac ttcggtgtag atggtgcgat ccatctggtc   64680
attgccgggg acttagactc aattgtgatc gggaagccta agaacgttcc taccatgacc   64740
ttgattacgt cacgcgacct acacctagta gaaggtggtc acgtattcgt gcaggataag   64800
gcaggcgagt tctacgtgca gatccagagt attactaaga ctgaaggcac cgccgatgtt   64860
tctccagagt ttacctacgt ggctaaaatc ctaggtactt tgactccggg gtacgtcgag   64920
tctactccag caacgtctac aggtcgtagt tcagcacgca agccagctgc cgctaacaag   64980
cctaagccgg gtaacaaaac tgcaagcaag ccagcggcta agaacccacc gcgctcacgt   65040
aagccacgtg gtcagaagcc agaaacaaag ccagcggaaa aggcggcgga gaacggctca   65100
aaaaacgcgg aagcggcaag cagtcaggaa ggcgcaaact aaccaaagct gacttgccag   65160
tggaccgctg gagagtagca ttcgatttga tgagtgccaa ttagtaaaac ctagggagct   65220
tcggctccct ttttcgtgcc taagtgccta ggtgttttcg acctaagtgc ctaggtagtt   65280
tgagcctaag tgcctaggta gtttgatcct aagtgcctag gctgtttagt aaaaaccacc   65340
cgatgccggg attcccgtga tcgggcagga agccccgccc cgtacagctt tccgctgaat   65400 ttacacccctt ttggtgatca cccccggaac tgaaaaatag ttcaaaaaac tgtttactat   65460
tagtaaaaac cgcgtatagt taaccgggta gacaaggagc acgcaacaat gcacaaacta   65520
cttgaaggct tcacgctatt actcgcctct ttactaatta tgggcggtga ttcaataata   65580
gacttagcct ataactttt tagtaattta ttttagtaaa ggtgttgact cactaaaaac   65640
agtttagtaa agttagcaac cagaaacacg gtcactcatt agtaagagga aaacggaaat   65700
gactaaacgc gcttcagaac ttgccaaaaa cactgctttt aacgatttgt tcgcttcaag   65760
caaaacgggc ttcaacgttg ccgaaatgaa agacggcgac aaggttaaga aagacttccg   65820
cacgtatgta atccacccgt cggcaattcg tgtaattgac ggctttaact cccgcatgga   65880
ttacggcgat attgaagagc tggcgatgag tcttaaagcc gagcacgaaa acaccgggca   65940
ggcacttatc caaccgttga tcttgatgtc ggttaagggc gagaaagaca cttacgatct   66000
tatcgctggg caccgtagaa ttatggcggt gcagtggttg tgggagaatc tacagtatga   66060
```

```
cgtgggcggc ttgatggctc gcatctacaa gtacgatacg ccttaccacc acatgatcgg   66120
cgttaacatg cgcgagaatg accaaaagcc actgttaccg attgaagagg cgatcaactt   66180
caagcgcctt aaagatgcgg attacacgct ggagcagatc cgagatctta gtggtcgctc   66240
aatctgtcat attagtaagc gtttaacgct tctaactggt gcggacgaag ttgtggacgc   66300
ggtagcatcc ggggaacttc aatcacaaat ggcggctgaa attgtcgtac gtcgtaaggg   66360
tgacatcgaa ggacaaaagg agcttgtcaa gaaagccacg gaaagcaagg aaggcaaccg   66420
cgctgtacgc cagcaactta aggcggaaat gaactcaacc ggacgcaaga acgcgctaa    66480 gaaagcggag aagaccgggg acaaaggcga cgttaaaaac aagcgcctaa ctcaaaaaga   66540
gcatgacgaa ttagtaacat ctcatgcgat gtgggcggct gactttgtga agacgtacgg   66600
tatcccggtt gatcaggtcg aagtcatgaa aaggcgggga gagttacgcg ctgaaggtga   66660
cgccgggtat cgtaagctta ctaagatgct tcaagaattt ggaaagattg acggaatcgc   66720
gcttgtgcta ggcatcgact tataaggtgc aagtttaacc gggtaatttc ggtagggagc   66780 tccccttat  tagctcccct ttttaaaggg cttccgtgtg gagtcttta  gaaagatata   66840 ccactgctag ccgggtaatt acggcagggc taccttacag cccactttt  aaagcgcatt   66900 tagtaaagtg cgttttaaca agtacaacaa tcggagtcag ataaatgcta ctagcaaaaa   66960
acctacagcg tgcgccttac cttaagactt taggcgatac ccttttcgct cactgcgtgc   67020
aggatctacc attcacggcg cttgataccg cgccagcctt cacccttact attactaagg   67080
gcggggacct agcaacagct cacacgctgg caatccgcga tgtggggag  gtccacgata   67140 tagcccgcca ctttaagacc ggggctaaac gcctacacgg aatccagatc tttaatgacc   67200
cgcttgctat cttttgagcag cacggcggtc acacgtggac cgggaaggcg atttataacg   67260
cgtttattgc caacagctca acactgggca agaaatggat caagcaagcg agcgcgtacg   67320
atattatgaa aactgtcaat accatcaatg atcgtgcgtt tagtgtatgg gtagaggaat   67380
tatgcgcaaa ggtggaagaa tgctaaaacg ctctataatc gccgctgtgc tgttttcag   67440 tgctaacatg gctcatggtg ccactgactg gcaaaacgtt caatctgacg cgtttgcggc   67500
gcgatttgcg gtacagtcaa tgattccttc tcgctgtatt tacccggaac gcttcaaccg   67560
cttctataaa tcggtgaagg ctgacggttt tgatactgct ttgcttaagg atgataaatt   67620
ccttactaag attaagcgcg agaaagctag tcttaaaaag tggctgggta caactgacga   67680
cggttgtgca atcattagca agcaattccc taaccagtac tacaagggat tcttttaaac   67740 tatttacta  attcggagac tcgaatcatg gcagaactac aacttcctaa cacaatcgcg   67800
gcagcggcta agaatctacc aaacgaagcg cgtgcaatcc tattgcagaa gtaccgcgac   67860
caagctaaga gcaagggctt aaactgggta tgctggctgt ttggtctaca gcacttctac   67920
caaggcaaga tcggaacggg tatcctcttc ctttgtctta tcccggtagg tgtaagcttt   67980
gtgtggtgga ttgttgaagc cttccgcaat aacaagcaga ttgaccgcta taacgacgcg   68040
ctggcaatgg agctgttcgc agagtctaag ctgctagcaa gcgactagct gaaaagccta   68100
agcacttctt actaataagc ctcggaatgt tccgggctt  ttttgatcgt ggatgcctag   68160
gcactttgaa aaattttgcc taggcacttt gaaaaattt  gcctaggcac tttgaaaaat   68220
tttacctagg cactttgaaa aattttacct aggaggtttg aaaaatttta cctaggaggt   68280
ttgaaaaatt ttgcctagga ggtttgagat tcggtggga  tttcggaccg ggtagatgtc   68340
aaaccacttg agaagatttt acatcttttc acttgacttg agatcttttt atactttttt   68400
aggttttctt ccgggcatag catagccggg atcattatta aacccttttt agtaaatttt   68460
```

```
atgttttcca cttccgccgg gaagcggtcc cggcgtggaa ggcgtcgcca gctggaccgg   68520
gaacccggca accgggcaac cgggcaaccg ggaaggcgtc cccgttgtgg tgcctattac   68580
cacaaattac ggatcaacta ccaaacaatt tttaatagtt tttagtaata agcatataac   68640
aatttaattt actaaaatga ttgaaggtgc ccgccgtttt tagtaaacgc gtgcgcccgg   68700
tctatttact gttagtaaaa aaataattgt tgaaagttta aaaaaggtat tgtaaccggg   68760
aacgggtttt agtaagatgt atcacaagga aggcgggaag ggttcccggc tatggcaaac   68820
aatggagcgc cgatcatgtt tatagatttg aacaaagttg cactacttcc caactttgat   68880
tggatgtttt ggaccgggat cgcgtgcgcc gcttatatcg tttggaaatt ctcaaaatga   68940
aaatattact aatatgcgcc gttatcgctg gcggtctagt atcatgcgat caagttatga   69000
cagctaacgc cgtgaaaacg tgcgaggcta aaaagcaagc cggggaattg tccgcacctt   69060
ttaacaattg tgatattttg aaattttagt aaaaataatt gttgaaagtt gcattttcct   69120
attgtacccg gaccgggttt ttagtaatat aaccatatcg aagcaaacaa acatttaagg   69180
ctgtcactta tgtttaaccg tcaaactcaa aaacaaaaga tcttttcgtt agcgtgggac   69240
aatgctcgcc acgctgcaaa cttccacggg ggcgagcccc gcgaatattt cgcggaatct   69300
ttaaagcttg cttaccgtgg cgtaaaactg gcaaacgtaa aaccacgatc tgaagttttc   69360
acactggatc tagttagcgc ggttttgtgt ggcatccttg caattgcaat aattctcttt   69420
tcaatctgga tcggtcatcc agcggctatt ctatccgcgc ttatcggttt ggcaatcggt   69480
gccgctggtt ggtctgattt cgaactacac ttgcaagaaa ttgcagaaaa caaacgaatc   69540
aataaacata ctaattttaa ccgtctagta attgactttt aagtaagggt atatcatgcg   69600
cgatttaaac aaatattttt caattgaaca aaaacttact aaccgcaccg aagcggtgaa   69660
cactgcaaac cgttttatta acgaagttgc gcccgttctg atcgcccgcc tatctgaagg   69720
ctttaagatc aaaaccacgt caaacgattt ctttaaaaag gatcacgaag acttgagatc   69780
aattctcgac aacgcagcga cggcgggcaa aatccatcaa gctttttttag atgtcactga   69840 caccgtgatc cgcgttcgcg tgaaaacaac gtttacagtt agtaacgttg gttgctgtta   69900
ctatgaggat ttcgctaata tttggagcct tgaaaaagat caggcatggg acttccagcc   69960
gctggagatt atcccggttg gaaaagtgat cgaggcacat caagcgatca agccacttga   70020
agatcagatc cgcgaactta agcgaaact atcacaactt aaatcaatta cgggcggct   70080 ataattatga atcttgagac ttcaatctac gcagcggata accgttacca cttttcggac   70140
cgctacgacg aacacggaac acttaacgat ctagcgtgtg agtacgcgga taagttccag   70200
tctgaatact tggagcacat caacggcgag accgccgatc ccgacgacgc tcaaacgtta   70260
gcgcatgatt acgcccgtga aacggtactt gacgggatgt gttggtggag tgttcgcttt   70320
ttcgcgatca cttacccgga tcagattttg aaccgtaaac cattcgatac gcttggagcc   70380
gaaacaccgg atcagctaat ccgccgaaat attgaggaag ttgtgaccgc cgccgccaac   70440
gtcctgatcg aagaaatgcg cgagcgtgga gatcttgacc gtgacgaata gcattgaagc   70500
attgacggat cgcggatacc ttccagccgg ggagtttaac ccggctattc ataaaaaggt   70560
tagtaaatgc gatttgggcg ggataccttg ccgcgtggtt agcggtcccg gcttggagcg   70620
cgggatcatg ccataccaca caacaaagat gatcggcggc ttcccggtag tggtagacaa   70680
taaaacatat tttgtaaaat cgaattagta agggcgttac tatgaaaaag gttaataaac   70740
cacaatcaaa ccgattcttt gaaggcgtgc gagatcttga cagcctgatc gggcgttcga   70800
```

```
ctcacaacgg cgaatactca aacaatgtga tccgtttagg gttcacacat ttaaacggtc   70860
aagtgttgga aggttgcccg gtttatatca ccggggaatt gttcgacaaa atcggcggga   70920
tggtttacgg caacggcggc gaactaaaca agcgttaccg cttggagatg gtttacacaa   70980
tgggcggcga atatcatctt tttgtcaagt accagcacat taacgatcg cgtcgtgttt    71040 gtgcaatatc cccggatagc gtccagcgat ggatcgacac gcaaccgaaa agcaattaat   71100
ttaaattcta ttagtaaggg cgcatttttgc gcccttttt gtacccgta agctgtacag    71160 ctttattact aatatttagc ttttgctgt acgtacaccg gggatctagg gcgattttc    71220 aatttggcgc gaaacgaagc ttttaatacc atagcaaggc ttttactaaa aaccgcttac   71280
aacgccatac agtgcgaatt tggggcatat tactaaaacg cgttttacta attactatta   71340
gtaaaaaccg ttataaaaat aattgttgaa agttggtttt tgctattgta ccgggaccgg   71400 gttttttagta atatgtatca caaggaaggc gggaaggggt cccggctaga ttgtgtggag  71460
tgctcgcaat ggcatcacaa aaacttgata ttttcccggc tcgcttgggt ttaccgtcgc   71520
aactaaacaa ggcttttaaa aaggcgggtt tatccgttgt aatcttggat aagcatccac   71580
gcggatcagt ttctagccgt ggcgatcaaa atttcgtttg ttaccgtgtt gatttaaat    71640 ccgttagtaa gtgcggcgat ggttccgacg ctcgcccggc ttcaatggca ttcactcaca   71700
acacaaaaac gcaccgcgtg acgttaacag aaatcgacta tctttaattt atatttttat   71760
cagtaagggc tttacaatga cagttactaa actagaagca ttaaaaacaa ctttcgatca   71820
agcggcaaac gcggcaatcg acgcgggcgc aactcattac attatcaata aaacgctgta   71880
cgcgggacaa tggatcacgt tctcttatag ttttgttaat tgcgacaaaa agaaacttaa   71940
tcaagttttt gaagttggga cgtatatcaa agagatgaaa acgtataaca gcactaaccg   72000
ctggatgtct gacaagtgga tcgggcataa cctagacggg cgcgaccgtc acggaatgat   72060
ccattctgaa ctattccaac ttaatcgcgg tattattaag taatcgcaca ataacaacta   72120
ttcacacatt tattagtaag ggcttattat gaaaactatt tgtaaagtta tcgcgggatc   72180
attcgctggc gagtttggtc gccttcattc taaattcagc acgggcttga tcatgctgga   72240
ggaccgccac ggcgatcagt tgtctgtcac tgaaaagcag atcgaacgct tggaagtgcg   72300
cacggctaac ctaaacaatc caactattca aggtttgatt gatattgatg gatctatcaa   72360
gtacggcttc aatagtggcg gctacgaatc aaacgcgtac tttatcacgg cggacggcgg   72420
cacgctggca attaatacag ttatcagtga gatcgataaa gttgatttct gcgacgactg   72480
cgatccgcaa tggcatattg tacaccacg cgtaaactat gaagagacgg atcttttaga   72540
ctctcacacg ggcgaaccaa tcccggcggc gtacagtgac gacgactaaa aacaattata   72600
ttagtaaggg cgcattttgc gccctttttt gtatccggga ccgcgtacag ctttattagt   72660
aaataactgc ttttcgctgt acgtacaccg gggatctagg gcgattttc aatttagggc    72720 gaaacgcggc ttttaatacc atagtaagga tattagtaaa aaccgcttaa aacgccatac   72780
agcgagaata agagctatat tactaaatcg cgtttacccg gtttaatatt agtaaaaacg   72840
ttctaaaaat aattgttgaa agttgcattt tcctattgta tccggtccgc taatttagta   72900
atatattcac acgtaagag attaccaata ttaatcattt tccccggtgg atttcccccg    72960
gtttatttag taagggctta ttatgaaaac tgttaaaatt actaattctg atttagtggc   73020
tattcgttca aagtttgatc gcgaacttca aaagcaaaaa gatcgctacg ctgcaaaccc   73080
ggatttgtac ggcaagcaaa cggaagaatc attgattcca cgttggatcg ataacgctta   73140
tagtaaagcc gtgttccaac aattggagcg cgacgggtta gcgtctatca ataaagaatc   73200
```

```
tgatcttttc tactcattcg cggatcatgc tggcgattgc ttcgatcctg aagttaataa    73260
agacatcgat ccggcggaat tgaaacgcca gcgtaaaaac gaattagcac gattcaaccg    73320
tcaaggcgta tactaccatg aattaattgt gctaggcgaa acgctaggat caatcggcgg    73380
ttttgttggg aatgactttt acggatcagg ctacgacatt gatttttaca acacggcgat    73440
cactcacatt gcgaacgtgt acggcggcga ctttatcccg acactagaca agatccagaa    73500
agcggaagaa taccgcgatt tagtaaaaga gtttgtttac tgcgattact caaaaacgat    73560
ccgtactaaa gcgaatcatt gcgttttgaa cctcgacgaa agatcgcgcc gttggattgt    73620
tgatattgat ccgggcgtgc cttcagaaat cgcggtactt gttttgagt tgttccatac    73680 atcgcatgat ttccgctggt gtacttcaga atctggaaag gctgatattc ttactaaaca    73740
cattcgcgca aacttgaaat aatcgggagt tactaaaatg caaaatgttt acggttatat    73800
ttatatgtct gttttttgtg aaactggttt aagcgagcgc ggcgcaaaaa ttgccgcctc    73860
ccgtgtgggc gcttcccaag tgggctatcg ttcaccgatc aataacatgt atattcaaac    73920
ggcggtaaag aatgccgccg gaaaatggga ggcgcgttaa aatggaggtt aagatcaccg    73980
ggcaaaatcc aatacataaa cacgtgtatt ctactttcta ccgtggcaaa cgcttcgacg    74040
tgaacacgct aacaaatagc gttactattg cgactttaa cgataagacg ggatcgcgct    74100
tcctcccggt taaatcttca gttactaaaa acaaagtatt gagcgccgta ctacaacaca    74160
tcgcaggcaa taaggatcaa taaaatgtca ttacgtggaa ttgcacaact gaaatcgaa    74220 tcatacaacg cgctgatcgt tctaatcgaa acggcgaac actcaaaagc gcgtgcaatg    74280
ttttgcgatt gggaccaatc aaaacaaagt cgttttatcc gtgcggttgg agatcttgaa    74340
ggcgtgacac ttgaattaca tcttgaaaca ttgaaacagt taattgtttt gtatgtttag    74400
caaatttaca ctgtaaacca ttatttatca ttttattagt aaggaaaagt tatcatgttt    74460
aatcaagtta ttgttgaaat tccagcgggc gagatcatca cggttgaaac ttataacacg    74520
ccatatcagg cacgcgggat cgctcgctgc attcaagcgg ttgcgggtac tgattaccaa    74580
ccgggcaaaa actattttgt tcacgttcca agttcacaaa tcaaccgcga cgcgttcgaa    74640
tacatcacgt ctattgattt agcaattatt gttagtgttg ctaatagtaa tccggcgggc    74700
gtcactgcaa ttgatgccga tcatcaggaa accgttaata gttttatcag ttggaacaac    74760
gatcaccgtc tagccgttga agcggataag cgcgaatcaa cacttgaaac acgcttacac    74820
aaatctaaat gctatcatca agcggtttac ttttggcgca accttccact aagtgagaaa    74880
aataatatta gtaaagtatt tccagcactg gcggacggct acccgcttga atcacaattt    74940
ggcggcattg ataaataact caataccact ttacactgta aattacttag taagagataa    75000
tcacactatg agtatcatga ttgaaataca caaggcggaa aatctagatc cagaaagttt    75060
cccgttatgc ccgtattgcg accaaccgat ccaaaacgta cacgacgcaa cgataatata    75120
taacggtatg ttttccgttt tggcactagc gcataaaaca tgccagcaag aaaacgaatc    75180
acaataatat caatagtgaa tacgcccggt ttaatcgccg ggcttttat tgtctatcgt    75240 ttactaataa cacattacta aatagtatca tttccccggt tgcccttccc ggttgtatcc    75300
gcccgccagc tatccacacg ccgccatttt ttcacctcga cataaacgcg ccgcgcaatc    75360
atatataatg ataaatctgt atataacaat tctccctagt gtgtaaatac tcattatcct    75420
atataggtag ttatccgtgt atattcttta tattatgtta tctgttatta gtgtatttat    75480
atcattatct ttcttactaa tacttttatc attttgcct atattcccca tctactgaag    75540
```

-continued

```
agtaaaaaga tagtaagcat tatatcaata gttaagcggt cattttgcgc cgtagaatcg  75600
ccgtattgag ccgtttatca atatacgggt atcattgccc tatttgagcg ccgcgcacgt  75660
cttacaacgc catacagcaa aacaatacac gtacaccatt atgcgccatt ttactaatat  75720
tgctgtacgt tcaatctata cccgcacgat tcccctatat acggaaatac acataaacgg  75780
cggttttccc tatatactag aaacattcac tatatacaat actatcatta acgccacgtt  75840
tacccggacc gattgaccgg gaccaaccga ccaacacgca aacgcaatga tacaactatc  75900
aatagactat tgagcattgc atcattaccc attccctatt gagcaatcgc attataaaca  75960
aatctattag taaacaattc tatcagttgc gcaattgata atagtgtcat tgagtaatct  76020
gtcagttgcg caattgagta atctatcaat aaggggtcc gaacccccca ccccccggca  76080
catattcgac gcttatcccc ggcacatatt cgacgcttat ccccggcaca tattcgacgc  76140
ttatccccgg cacatattcg acgcttatcc ccggcacata ttcgacg              76187
```

VIBRIO PARAHAEMOLYTICUS BACTERIOPHAGE VIB-PAP-7 AND USE OF SAME FOR INHIBITING VIBRIO PARAHAEMOLYTICUS BACTERIA PROLIFERATION

CROSS-REFERENCE TO RELATED APPLICATIONS

This application is a U.S. National Phase Application of International Application No. PCT/KR2018/002734, filed Mar. 8, 2018, which claims priority to Korean Application No. 10-2017-0058068, filed May 10, 2017, each of which are hereby incorporated by reference in their entirety.

REFFERENCE TO SEQUENCE LISTING

The Sequence Listing submitted Nov. 8, 2019, as a text file named "08162_0063U1_Sequence_Listing.txt," created on Nov. 7, 2019, and having a size of 96,996 bytes is hereby incorporated by reference pursuant to 37 C.F.R. § 1.52(e)(5).

TECHNICAL FIELD

The present invention relates to a bacteriophage isolated from nature, which is capable of infecting *Vibrio parahaemolyticus* to thus kill *Vibrio parahaemolyticus*, and a method of preventing or treating a disease caused by *Vibrio parahaemolyticus* using a composition containing the above bacteriophage as an active ingredient. More particularly, the present invention relates to a Myoviridae bacteriophage Vib-PAP-7 (Accession number: KCTC 13247BP) isolated from nature, which has the ability to kill *Vibrio parahaemolyticus* and has the genome represented by SEQ ID NO: 1, and a method of preventing or treating a disease caused by *Vibrio parahaemolyticus* using a composition containing the above bacteriophage as an active ingredient.

BACKGROUND ART

*Vibrio parahaemolyticus*, belonging to the genus *Vibrio*, is a facultative anaerobe having peritrichous flagellum, and is a gram-negative bacterium. *Vibrio parahaemolyticus* is a marine organism that is widely detected in brackish water regions or coastal seawater and in marine products all over the world, and is known as the main cause of bacterial food poisoning associated with seafood intake. Most *Vibrio parahaemolyticus* are non-pathogenic, and only *Vibrio parahaemolyticus*, exhibiting a hemolytic phenomenon, is pathogenic. *Vibrio parahaemolyticus* bacteria are serologically classified based on 75 types of capsular antigens (K) and 13 types of somatic antigens (O), and flagella antigens (H) are present in all *Vibrio parahaemolyticus* bacteria. Therefore, the serotypes of *Vibrio parahaemolyticus* are classified depending on the type of K and O antigens.

*Vibrio parahaemolyticus* causes serious economic damage in the aquaculture industry by causing vibriosis in various fishes and shellfishes. In particular, outbreaks of vibriosis in fish caused by *Vibrio parahaemolyticus* infection occur frequently, resulting in great economic damage. Therefore, there is urgent need to develop methods that are applicable for preventing and further treating a *Vibrio parahaemolyticus* infection.

Although various antibiotics have been used for the prevention or treatment of diseases caused by *Vibrio parahaemolyticus*, the incidence of bacteria resistant to known antibiotics is increasing these days, and thus the development of other methods besides antibiotics is urgently required.

Recently, the use of bacteriophages as a countermeasure against infectious bacterial diseases has attracted considerable attention. In particular, these bacteriophages are receiving great attention due to strong antibacterial activity against antibiotic-resistant bacteria. Bacteriophages are very small microorganisms infecting bacteria, and are usually simply called "phages". Once a bacteriophage infects a bacterium, the bacteriophage is proliferated inside the bacterial cell. After proliferation, the progeny of the bacteriophage destroy the bacterial cell wall and escape from the host bacteria, demonstrating that the bacteriophage has the ability to kill bacteria. The manner in which the bacteriophage infects bacteria is characterized by very high specificity thereof, and thus the range of types of bacteriophages that may infect specific bacteria is limited. That is, a certain bacteriophage may infect only a specific bacterium, suggesting that a certain bacteriophage is capable of providing an antibacterial effect only for a specific bacterium. Due to this bacterial specificity of bacteriophages, the bacteriophage confers antibacterial effects only upon target bacteria, but does not affect commensal bacteria in the environment or in the interiors of animals. Conventional antibiotics, which have been widely used for bacterial treatment, incidentally influence many other kinds of bacteria. This causes problems such as environmental pollution and the disturbance of normal flora in animals. In contrast, the use of bacteriophages does not disturb normal flora in animals, because the target bacterium is selectively killed by use of bacteriophages. Hence, bacteriophages may be utilized safely, which thus greatly lessens the probability of adverse effects of use thereof compared to antibiotics.

Bacteriophages were first discovered by the English bacteriologist Twort in 1915 when he noticed that *Micrococcus* colonies softened and became transparent due to something unknown. In 1917, the French bacteriologist d'Herelle discovered that *Shigella dysenteriae* in the filtrate of dysentery patient feces was destroyed by something, and further studied this phenomenon. As a result, he independently identified bacteriophages, and named them bacteriophages, which means "eater of bacteria". Since then, bacteriophages acting against such pathogenic bacteria as *Shigella, Salmonella Typhi*, and *Vibrio cholerae* have been continually identified.

Owing to the unique ability of bacteriophages to kill bacteria, bacteriophages have attracted attention as a potentially effective countermeasure against bacterial infection since their discovery, and a lot of research related thereto has been conducted. However, since penicillin was discovered by Fleming, studies on bacteriophages have continued only in some Eastern European countries and in the former Soviet Union, because the spread of antibiotics was generalized. Since 2000, limitations of conventional antibiotics have become apparent due to the increase in antibiotic-resistant bacteria, and the possibility of developing bacteriophages as a substitute for conventional antibiotics has been highlighted, and thus bacteriophages are again attracting attention as antibacterial agents.

As demonstrated above, bacteriophages tend to be highly specific for target bacteria. Because of the high specificity of bacteriophages to bacteria, bacteriophages frequently exhibit an antibacterial effect only for certain strains of bacteria, even within the same species. In addition, the antibacterial strength of bacteriophages may vary depending on the target bacterial strain. Therefore, it is necessary to collect many kinds of bacteriophages that are useful in order to effectively control specific bacteria. Hence, in order to develop an effective bacteriophage utilization method for controlling *Vibrio parahaemolyticus*, many kinds of bacteriophages that exhibit antibacterial action against *Vibrio parahaemolyticus* must be acquired. Furthermore, the resulting bacteriophages need to be screened as to whether or not they are superior to others in view of the aspects of antibacterial strength and spectrum.

DISCLOSURE

Technical Problem

Therefore, the present inventors endeavored to develop a composition for use in the prevention or treatment of a disease caused by *Vibrio parahaemolyticus* using a bacteriophage that is isolated from nature and is capable of killing *Vibrio parahaemolyticus*, and further to establish a method of preventing or treating a disease caused by *Vibrio parahaemolyticus* using the composition. As a result, the present inventors isolated a bacteriophage suitable for this purpose from nature and determined the sequence of the genome, which distinguishes the isolated bacteriophage from other bacteriophages. Then, the present inventors developed a composition containing the bacteriophage as an active ingredient, and ascertained that this composition is capable of being effectively used to prevent or treat a disease caused by *Vibrio parahaemolyticus*, thus culminating in the present invention.

Accordingly, it is an object of the present invention to provide a Myoviridae bacteriophage Vib-PAP-7 (Accession number: KCTC 13247BP) isolated from nature, which has the ability to specifically kill *Vibrio parahaemolyticus* and has the genome represented by SEQ ID NO: 1.

It is another object of the present invention to provide a composition for use in the prevention or treatment of a disease caused by *Vibrio parahaemolyticus*, which contains, as an active ingredient, an isolated bacteriophage Vib-PAP-7 (Accession number: KCTC 13247BP) infecting *Vibrio parahaemolyticus* to thus kill *Vibrio parahaemolyticus*.

It is another object of the present invention to provide a method of preventing or treating a disease caused by *Vibrio parahaemolyticus* using the composition for the prevention or treatment of a disease caused by *Vibrio parahaemolyticus*, which contains, as an active ingredient, the isolated bacteriophage Vib-PAP-7 (Accession number: KCTC 13247BP) infecting *Vibrio parahaemolyticus* to thus kill *Vibrio parahaemolyticus*.

It is another object of the present invention to provide a medicine bath agent (immersion agent) for the prevention or treatment of a disease caused by *Vibrio parahaemolyticus* using the said composition.

It is another object of the present invention to provide a feed additive effective upon farming by preventing or treating a disease caused by *Vibrio parahaemolyticus* using the said composition.

Technical Solution

The present invention provides a Myoviridae bacteriophage Vib-PAP-7 (Accession number: KCTC 13247BP) isolated from nature, which has the ability to specifically kill *Vibrio parahaemolyticus* and has the genome represented by SEQ ID NO: 1, and a method of preventing or treating a disease caused by *Vibrio parahaemolyticus* using a composition containing the Myoviridae bacteriophage Vib-PAP-7 as an active ingredient.

The bacteriophage Vib-PAP-7 was isolated by the present inventors and then deposited under the Budapest Treaty on the International Procedure at Korean Collection for Type Cultures, Korea Research Institute of Bioscience and Biotechnology (KRIBB), 125 Gwahak-ro, Yuseong-gu, Daijeon 305-806, Republic of Korea; the deposit was made on Apr. 12, 2017 (Accession number: KCTC 13247BP).

The present invention also provides a medicine bath agent and a feed additive for use in the prevention or treatment of a disease caused by *Vibrio parahaemolyticus*, each of which contain the bacteriophage Vib-PAP-7 as an active ingredient.

Since the bacteriophage Vib-PAP-7 contained in the composition of the present invention effectively kills *Vibrio parahaemolyticus*, it is effective in the prevention (prevention of infection) or treatment (treatment of infection) of a disease caused by *Vibrio parahaemolyticus*. Therefore, the composition of the present invention is capable of being utilized for the prevention and treatment of a disease caused by *Vibrio parahaemolyticus*.

As used herein, the terms "prevention" and "prevent" refer to (i) prevention of a *Vibrio parahaemolyticus* infection and (ii) inhibition of the development of a disease caused by a *Vibrio parahaemolyticus* infection.

As used herein, the terms "treatment" and "treat" refer to all actions that (i) suppress a disease caused by *Vibrio parahaemolyticus* and (ii) alleviate the pathological condition of the disease caused by *Vibrio parahaemolyticus*.

As used herein, the terms "isolate", "isolating", and "isolated" refer to actions that isolate bacteriophages from nature by using various experimental techniques and that secure characteristics that distinguish the bacteriophage of the present invention from others, and further include the action of proliferating the bacteriophage of the present invention using bioengineering techniques so that the bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may further include lubricants, wetting agents, sweeteners, flavors, emulsifiers, suspension agents, and preservatives, in addition to the above ingredients.

The bacteriophage Vib-PAP-7 is contained as an active ingredient in the composition of the present invention. The bacteriophage Vib-PAP-7 is contained at a concentration of $1 \times 10^1$ pfu/ml to $1 \times 10^{30}$ pfu/ml or $1 \times 10^1$ pfu/g to $1 \times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention may be formulated using a pharmaceutically acceptable carrier and/or excipient in accordance with a method that may be easily carried out by those skilled in the art to which the present invention belongs, in order to prepare the same in a unit dosage form or insert the same into a multiple-dose container. Here, the formulation thereof may be provided in the form of a solution, a suspension, or an emulsion in an oil or aqueous medium, or in the form of an extract, a powder, a granule, a tablet, or a capsule, and may additionally contain a dispersant or a stabilizer.

The composition of the present invention may be prepared as a medicine bath agent or a feed additive depending on the end use thereof, without limitation thereto. In order to improve the effectiveness thereof, bacteriophages that confer antibacterial activity against other bacterial species may be further included in the composition of the present invention. In addition, other kinds of bacteriophages that have antibacterial activity against *Vibrio parahaemolyticus* may be further included in the composition of the present invention. These bacteriophages may be combined appropriately so as to maximize the antibacterial effects thereof, because their antibacterial activities against *Vibrio parahaemolyticus* may vary from the aspects of antibacterial strength and spectrum.

Advantageous Effects

According to the present invention, the method of preventing or treating a disease caused by *Vibrio parahaemolyticus* using the composition containing the bacteriophage Vib-PAP-7 as an active ingredient is advantageous because of very high specificity for *Vibrio parahaemolyticus* compared to conventional methods based on existing antibiotics. This means that the composition of the present invention can be used for the prevention or treatment of a disease caused by *Vibrio parahaemolyticus* without affecting other useful commensal bacteria, and has fewer side effects attributable to the use thereof. Typically, when antibiotics are used, commensal bacteria are also damaged, ultimately lowering the immunity of animals and thus entailing various side effects owing to the use thereof. Meanwhile, in the case of various bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the various strains of bacteria belonging to *Vibrio parahaemolyticus*, bacteriophages usually being effective only on some bacterial strains, even within the same species, and the antibacterial activity of bacteriophages thus depending on the bacterial strain even for the same species of bacteria]. Accordingly, the present invention can provide antibacterial activity against *Vibrio parahaemolyticus* discriminating from that of other bacteriophages acting on *Vibrio parahaemolyticus*. This provides a great variety of effects in applicability to industrial fields.

DESCRIPTION OF DRAWINGS

FIG. 1 is an electron micrograph showing the morphology of the bacteriophage Vib-PAP-7.

FIG. 2 is a photograph showing results of experiment of the ability of the bacteriophage Vib-PAP-7 to kill *Vibrio parahaemolyticus*. Based on the center line of the plate culture medium, only the buffer containing no bacteriophage Vib-PAP-7 is spotted on the left side thereof and a solution containing the bacteriophage Vib-PAP-7 is spotted on the right side thereof. The clear zone observed on the right side is a plaque formed by lysis of the target bacteria due to the action of the bacteriophage Vib-PAP-7.

MODE FOR INVENTION

A better understanding of the present invention will be given through the following examples. These examples are merely set forth to illustrate the present invention but are not to be construed as limiting the scope of the present invention.

Example 1: Isolation of Bacteriophage Capable of Killing *Vibrio parahaemolyticus*

Samples were collected from nature to isolate the bacteriophage capable of killing 5/7/i Vibrio parahaemolyticus. Here, the Vibrio parahaemolyticus strains used for the bacteriophage isolation are *Vibrio parahaemolyticus* that had been previously isolated and identified as *Vibrio parahaemolyticus* by the present inventors.

The procedure for isolating the bacteriophage is described in detail herein below. The collected sample was added to LB (Luria-Bertani) culture medium (tryptone, 10 g/L; yeast extract, 5 g/L; sodium chloride, 10 g/L) inoculated with *Vibrio parahaemolyticus* at a ratio of 1/1,000, followed by shaking culture at 37° C. for 3 to 4 hr. Thereafter, centrifugation was performed at 8,000 rpm for 20 min and a supernatant was recovered. The recovered supernatant was inoculated with *Vibrio parahaemolyticus* at a ratio of 1/1,000 and then subjected to shaking culture at 37° C. for 3 to 4 hr. When the sample contained the bacteriophage, the above procedure was repeated a total of 5 times in order to sufficiently increase the number (titer) of bacteriophages. After repeating the procedure 5 times, the culture broth was subjected to centrifugation at 8,000 rpm for 20 min. Thereafter, the recovered supernatant was filtered using a 0.45 μm filter. The filtrate thus obtained was used in a typical spot assay for evaluating whether or not a bacteriophage capable of killing *Vibrio parahaemolyticus* was included therein.

The spot assay was performed as follows: LB culture medium was inoculated with *Vibrio parahaemolyticus* at a ratio of 1/1,000 and then subjected to shaking culture at 37° C. overnight. 3 ml ($OD_{600}$ of 1.5) of the culture broth of *Vibrio parahaemolyticus* prepared above was spread on LA (Luria-Bertani Agar: tryptone, 10 g/L; yeast extract, 5 g/L; sodium chloride, 10 g/L; agar, 15 g/L) plate. The plate was left on a clean bench for about 30 min to dry the spread solution. After drying, 10 μl of the prepared filtrate was spotted onto the plate which *Vibrio parahaemolyticus* was spread and then left for about 30 min to dry. Thereafter, the plate that was subjected to spotting was standing-cultured at 37° C. for one day, and then examined for the formation of clear zones at the positions where the filtrate was dropped. In the case in which the filtrate generated a clear zone, it was judged that a bacteriophage capable of killing *Vibrio parahaemolyticus* was included therein. Through the above examination, it was possible to obtain a filtrate containing a bacteriophage having the ability to kill *Vibrio parahaemolyticus*.

The pure bacteriophage was isolated from the filtrate confirmed above to have the bacteriophage capable of killing *Vibrio parahaemolyticus*. A typical plaque assay was used to isolate the pure bacteriophage. In detail, a plaque formed in the course of the plaque assay was recovered using a sterilized tip, added to the culture broth of *Vibrio parahaemolyticus*, and then cultured at 37° C. for 4 to 5 hr. Thereafter, centrifugation was performed at 8,000 rpm for 20 min to obtain a supernatant. The culture broth of *Vibrio parahaemolyticus* was added to the obtained supernatant at a volume ratio of 1/50 and then cultured at 37° C. for 4 to 5 hr. In order to increase the number of bacteriophages, the above procedure was repeated at least 5 times. Then, centrifugation was performed at 8,000 rpm for 20 min in order to obtain the final supernatant. A plaque assay was further performed using the final supernatant thus obtained. In general, isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for isolating the pure bacteriophage was repeated in its entirety until the generated plaques became similar to each other with respect to size and morphology. In addition, final isolation of the pure bacteriophage was confirmed using electron microscopy. The above procedure was repeated until the isolation of the pure bacteriophage was confirmed using electron microscopy. The electron microscopy was performed through a typical method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics thereof, the above bacteriophage was confirmed to belong to the Myoviridae bacteriophage.

The solution containing the pure bacteriophage confirmed above was subjected to the following purification process. The culture broth of *Vibrio parahaemolyticus* was added to the solution containing the pure bacteriophage at a volume ratio of 1/50 based on the total volume of the bacteriophage solution, and then further cultured for 4 to 5 hr. Thereafter, centrifugation was performed at 8,000 rpm for 20 min to obtain a supernatant. This procedure was repeated a total of 5 times in order to obtain a solution containing a sufficient number of bacteriophages. The supernatant obtained from the final centrifugation was filtered using a 0.45 μm filter, followed by a typical polyethylene glycol (PEG) precipitation process. Specifically, PEG and NaCl were added to 100 ml of the filtrate reaching 10% PEG 8000/0.5 M NaCl, which was then allowed to stand at 4° C. for 2 to 3 hr. Thereafter, centrifugation was performed at 8,000 rpm for 30 min to obtain a bacteriophage precipitate. The bacteriophage precipitate thus obtained was suspended in 5 ml of a buffer (10 mM Tris-HCl, 10 mM $MgSO_4$, 0.1% gelatin, pH 8.0). The resulting material may be referred to as a bacteriophage suspension or bacteriophage solution.

As a result, the pure bacteriophage purified above was collected, was named Vib-PAP-7, and deposited at the Korean Collection for Type Cultures, Korea Research Institute of Bioscience and Biotechnology on Apr. 12, 2017 (Accession number: KCTC 13247BP).

Example 2: Separation and Sequence Analysis of Genome of Bacteriophage Vib-PAP-7

The genome of the bacteriophage Vib-PAP-7 was separated as follows. The genome was separated from the bacteriophage suspension obtained using the same method as in Example 1. First, in order to eliminate DNA and RNA of *Vibrio parahaemolyticus* included in the suspension, 200 U of each of DNase I and RNase A was added to 10 ml of the bacteriophage suspension and then allowed to stand at 37° C. for 30 min. After being allowed to stand for 30 min, in order to inactivate the DNase I and RNase A activity, 500 μl of 0.5 M ethylenediaminetetraacetic acid (EDTA) was added thereto, and the resulting mixture was then allowed to stand for 10 min. In addition, the resulting mixture was further allowed to stand at 65° C. for 10 min, and 100 μl of proteinase K (20 mg/ml) was then added thereto so as to break the outer wall of the bacteriophage, followed by reacting at 37° C. for 20 min. Thereafter, 500 μl of 10% sodium dodecyl sulfate (SDS) was added thereto, followed by reacting at 65° C. for 1 hr. After reaction for 1 hr, the resulting reaction solution was added with 10 ml of the solution of phenol:chloroform:isoamyl alcohol, which were mixed at a component ratio of 25:24:1, followed by mixing thoroughly. In addition, the resulting mixture was subjected to centrifugation at 13,000 rpm for 15 min to separate layers. Among the separated layers, the upper layer was selected, and isopropyl alcohol was added thereto at a volume ratio of 1.5, followed by centrifugation at 13,000 rpm for 10 min to precipitate the genome. After collecting the precipitate, 70% ethanol was added to the precipitate, followed by centrifugation at 13,000 rpm for 10 min to wash the precipitate. The washed precipitate was recovered, vacuum-dried and then dissolved in 100 μl of water. This procedure was repeated to obtain a sufficient amount of the genome of the bacteriophage Vib-PAP-7.

Information on the sequence of the genome of the bacteriophage Vib-PAP-7 thus obtained was secured by performing next-generation sequencing analysis using an Illumina Mi-Seq apparatus provided by the Macrogen. The finally analyzed genome of the bacteriophage Vib-PAP-7 had a size of 76,187 bp, and the whole genome sequence is represented by SEQ ID NO: 1.

The homology (similarity) of the bacteriophage Vib-PAP-7 genomic sequence obtained above with conventionally reported bacteriophage genomic sequences was investigated using BLAST on the web. Based on the results of the BLAST investigation, the genomic sequence of the bacteriophage Vib-PAP-7 was found to have relatively high homology with the sequence of the *Vibrio* bacteriophage SSP002 (GenBank Accession No. JQ692107.1) and the sequence of vB_VpaS_MAR10 (GenBank Accession No. JX556418.1) (96%/97% and 67%/79%, respectively, in the order of query coverage/identity). However, the number of open reading frames (ORFs) on the bacteriophage Vib-PAP-7 genome is 101, whereas the bacteriophage SSP002 has 102 open reading frames and the bacteriophage vB-VpaS_MAR10, having slightly low homology therewith, has 104 open reading frames, from which these bacteriophages are also evaluated to be different.

Therefore, it can be concluded that the bacteriophage Vib-PAP-7 is a novel bacteriophage different from existing reported bacteriophages. Moreover, since the antibacterial strength and spectrum of bacteriophages typically depend on the type of bacteriophage, it is considered that the bacteriophage Vib-PAP-7 can provide antibacterial activity different from that of any other bacteriophages reported conventionally.

Example 3: Investigation of Killing Ability of Bacteriophage Vib-PAP-7 for *Vibrio parahaemolyticus*

The killing ability of the isolated bacteriophage Vib-PAP-7 for *Vibrio parahaemolyticus* was investigated. In order to evaluate the killing ability, the formation of clear zones was observed using a spot assay in the same manner as described in connection with Example 1. A total of 25 *Vibrio parahaemolyticus* strains were used for the investigation of killing ability, and were obtained from a strain bank or were isolated and identified as *Vibrio parahaemolyticus* by the present inventors. The bacteriophage Vib-PAP-7 had the ability to kill a total of 21 strains, among 25 strains of *Vibrio parahaemolyticus*, that is, the experimental target. The representative experimental results thereof are shown in FIG. 2. Meanwhile, the ability of the bacteriophage Vib-PAP-7 to kill *Edwardsiella tarda, Vibrio anguillarum, Vibrio ichthyoenteri, Lactococcus garvieae, Streptococcus parauberis, Streptococcus iniae,* and *Aeromonas salmoni-*

*cida* was also measured. Consequently, the bacteriophage Vib-PAP-7 did not have the ability to kill these microorganisms.

Therefore, it can be concluded that the bacteriophage Vib-PAP-7 has high ability to kill *Vibrio parahaemolyticus* and an antibacterial effect against many *Vibrio parahaemolyticus* strains, indicating that the bacteriophage Vib-PAP-7 can be used as an active ingredient of the composition for preventing or treating diseases caused by *Vibrio parahaemolyticus*.

Example 4: Experiment for Prevention of *Vibrio Parahaemolyticus* Infection Using Bacteriophage Vib-PAP-7

100 μl of a bacteriophage Vib-PAP-7 solution at a level of $1\times10^8$ pfu/ml was added to a tube containing 9 ml of LB culture medium. To another tube containing 9 ml of LB culture medium, only the same amount of LB culture medium was further added. A culture broth of *Vibrio parahaemolyticus* was then added to each tube so that absorbance reached about 0.5 at 600 nm. After the addition of *Vibrio parahaemolyticus*, the tubes were transferred to an incubator at 37° C., followed by shaking culture, during which the growth of *Vibrio parahaemolyticus* was observed. As shown in Table 1 below, it was observed that the growth of *Vibrio parahaemolyticus* was inhibited in the tube to which the bacteriophage Vib-PAP-7 solution was added, whereas the growth of *Vibrio parahaemolyticus* was not inhibited in the tube to which the bacteriophage solution was not added.

TABLE 1

Growth inhibition of *Vibrio parahaemolyticus*

| | $OD_{600}$ absorbance value | | |
|---|---|---|---|
| Classification | 0 min after culture | 60 min after culture | 120 min after culture |
| Not added with bacteriophage solution | 0.52 | 1.18 | 1.56 |
| Added with bacteriophage solution | 0.52 | 0.23 | 0.19 |

The above results show that the bacteriophage Vib-PAP-7 of the present invention is not only capable of inhibiting the growth of *Vibrio parahaemolyticus* but also capable of killing *Vibrio parahaemolyticus*. Therefore, it is concluded that the bacteriophage Vib-PAP-7 can be used as an active ingredient of the composition for preventing diseases caused by *Vibrio parahaemolyticus*.

Example 5: Animal Testing for Preventing Disease Caused by *Vibrio parahaemolyticus* Using Bacteriophage Vib-PAP-7

A total of 2 groups of sixty juvenile sea bass per group (body weight: 5 to 7 g and body length: 8 to 10 cm) were prepared and farmed separately in water tanks, and an experiment was performed for 14 days. The environment surrounding the water tanks was controlled, and the temperature in the laboratory where the water tanks were located was maintained constant. Over the whole experimental period from the 1st day of the experiment, sea bass in an experimental group (the group to which the bacteriophage was administered) were fed with a feed containing the bacteriophage Vib-PAP-7 at $1\times10^8$ pfu/g in a typical feeding manner. In contrast, sea bass in a control group (the group to which the bacteriophage was not administered) were fed with the same feed as the experimental group except that the bacteriophage Vib-PAP-7 was not contained in the same manner as in the experimental group. For 2 days from the 7th day after the experiment started, the provided feed was added with *Vibrio parahaemolyticus* at a level of $1\times10^8$ cfu/g and then provided respectively twice a day so as to induce a *Vibrio parahaemolyticus* infection. From the 9th day after the experiment started (the $2^{nd}$ day after the *Vibrio parahaemolyticus* infection was induced), vibriosis pathogenesis was examined in all test animals on a daily basis. The vibriosis pathogenesis was evaluated by measuring a body-darkening index. The measurement of the body-darkening index was performed using a typical process of measuring a dark coloration (DC) score (0: normal, 1: slight darkening, 2: strong darkening). The results are shown in Table 2 below.

TABLE 2

Result of measurement of body-darkening index (mean)

| | DC score (mean) | | | | | |
|---|---|---|---|---|---|---|
| Days | D 9 | D 10 | D 11 | D 12 | D 13 | D 14 |
| Control group (not administered with bacteriophage) | 0.68 | 0.72 | 0.84 | 0.88 | 1.00 | 1.12 |
| Experimental group (administered with bacteriophage) | 0.32 | 0.12 | 0.04 | 0.04 | 0 | 0 |

As is apparent from the above results, it can be concluded that the bacteriophage Vib-PAP-7 of the present invention is very effective in the prevention of diseases caused by *Vibrio parahaemolyticus*.

Example 6: Treatment of Disease Caused by *Vibrio parahaemolyticus* Using Bacteriophage Vib-PAP-7

The therapeutic effect of the bacteriophage Vib-PAP-7 on diseases caused by *Vibrio parahaemolyticus* was evaluated as follows. A total of 2 groups of sixty juvenile sea bass per group (body weight: 5 to 7 g and body length: 8 to 10 cm) were prepared and farmed separately in water tanks, and an experiment was performed for 14 days. The environment surrounding the water tanks was controlled, and the temperature in the laboratory where the water tanks were located was maintained constant. For 3 days from the 5th day after the experiment started, the feed contaminated with *Vibrio parahaemolyticus* at a level of $1\times10^8$ cfu/g was provided twice a day in a typical feeding manner. Sea bass subjects showing clinical symptoms of vibriosis were observed in both water tanks from the last day of the procedure in which the feed contaminated with *Vibrio parahaemolyticus* was provided. From the next day after the feed contaminated with *Vibrio parahaemolyticus* was provided for 3 days (the 8th day after the experiment started), sea bass in an experimental group (the group to which the bacteriophage was administered) were fed with a feed containing the bacteriophage Vib-PAP-7 ($1\times10^8$ pfu/g) in a typical feeding manner. In contrast, sea bass in a control group (the group to which the bacteriophage was not administered) were fed with the same feed as the experimental group except that the bacteriophage Vib-PAP-7 was not contained in the same manner as in the experimental group. From the 3/d day after the forced infection of *Vibrio parahaemolyticus* (the 8th day after the experiment started), vibriosis pathogenesis was examined in all test animals on a daily basis. The vibriosis pathogenesis caused by *Vibrio parahaemolyticus* was examined by measuring a body-darkening index as in Example 5. The results are shown in Table 3 below.

TABLE 3

Result of measurement of body-darkening index (mean)

| Days | DC score (mean) | | | | | | |
|---|---|---|---|---|---|---|---|
| | D 8 | D 9 | D 10 | D 11 | D 12 | D 13 | D 14 |
| Control group (not administered with bacteriophage) | 0.87 | 0.93 | 1.03 | 1.13 | 1.13 | 1.30 | 1.37 |
| Experimental group (administered with bacteriophage) | 0.90 | 0.87 | 0.83 | 0.70 | 0.37 | 0.13 | 0.13 |

As is apparent from the above results, it can be concluded that the bacteriophage Vib-PAP-7 of the present invention is very effective in the treatment of diseases caused by *Vibrio parahaemolyticus*.

Example 7: Preparation of Feed Additives and Feeds

Feed additives were prepared using a bacteriophage Vib-PAP-7 solution so that a bacteriophage Vib-PAP-7 was contained in an amount of $1\times10^8$ pfu for 1 g of the feed additives. The method of preparing the feed additive was as follows: Maltodextrin (50%, w/v) was added to the bacteriophage solution, and the resulting mixture was then freeze-dried. Finally, the dried mixture was ground into fine powder. In the above-described preparation procedure, the drying process may be replaced with drying under reduced pressure, drying with heat, or drying at room temperature. In order to prepare the control for comparison, a feed additive was prepared that did not contain the bacteriophage but contained the buffer (10 mM Tris-HCl, 10 mM $MgSO_4$, 0.1% gelatin, pH 8.0) used to prepare the bacteriophage solution.

The two kinds of feed additives thus prepared were each mixed with a raw fish-based moist pellet at a weight ratio of 250, thus ultimately preparing two kinds of final feeds.

Example 8: Preparation of Medicine Bath Agent

The method of preparing a medicine bath agent was as follows: The medicine bath agent was prepared using a bacteriophage Vib-PAP-7 solution so that a bacteriophage Vib-PAP-7 was contained in an amount of $1\times10^8$ pfu for 1 ml of the medicine bath agent. In the method of preparing the medicine bath agent, the bacteriophage Vib-PAP-7 solution was added so that the bacteriophage Vib-PAP-7 was contained in an amount of $1\times10^8$ pfu for 1 ml of a buffer used to prepare the bacteriophage solution, and mixing was sufficiently performed. In order to prepare the control for comparison, the buffer used to prepare the bacteriophage solution was used as the medicine bath agent that did not contain the bacteriophage.

The two kinds of medicine bath agents thus prepared were diluted with water at a volume ratio of 1,000, resulting in the final medicine bath agent.

Example 9: Confirmation of Feeding Effect on Sea Bass Farming

The improvement in the feeding result upon sea bass farming was investigated using the feeds and the medicine bath agents prepared in Examples 7 and 8. In particular, the investigation was focused on mortality ratio. A total of 1,000 juvenile sea bass were divided into two groups, each including 500 sea bass (group A: fed with the feed; and group B: treated with the medicine bath agent), and an experiment was performed for 4 weeks. Each group was further divided into subgroups each including 250 sea bass, and the subgroups were classified into a subgroup to which the bacteriophage Vib-PAP-7 was applied (subgroup-①) and a subgroup to which the bacteriophage was not applied (subgroup-②). In the present experiment, the target sea bass was juvenile (body weight: 5 to 7 g and body length: 8 to 10 cm), and the juvenile sea bass of the experimental subgroups were farmed in separate water tanks spaced apart from each other at a certain interval. The subgroups were classified and named as shown in Table 4 below.

TABLE 4

Sub-group classification and expression in sea bass feeding experiment

| | Sub-group classification and expression | |
|---|---|---|
| Application | Bacteriophage Vib-PAP-7 is applied | Bacteriophage is not applied |
| Group fed with feed | A-① | A-② |
| Group treated with medicine bath agent | B-① | B-② |

In the case of provision of the feeds, the feeds prepared in Example 7 were provided according to conventional feeding method as classified in Table 4. The treatment using the medicine bath agent was performed according to a conventional treatment method using a medicine bath agent, in which fish bodies are immersed in a diluted solution of the medicine bath agent, as classified in Table 4 using the medicine bath agent prepared as described in Example 8. The results are shown in Table 5.

TABLE 5

Mortality ratio of sea bass in feeding experiment

| Group | Dead sea bass/total sea bass of experiment (No.) | Mortality ratio (%) |
|---|---|---|
| A-① | 7/250 | 2.8 |
| A-② | 43/250 | 17.2 |
| B-① | 11/250 | 4.4 |
| B-② | 56/250 | 22.4 |

The above results indicate that the provision of the feed prepared according to the present invention and the treatment using the medicine bath agent prepared according to the present invention were effective at reducing mortality ratio in the farming of sea bass. Therefore, it is concluded that the composition of the present invention could be efficiently applied to improving the results of feeding of sea bass.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

[Accession Number]
Name of Depositary Authority: KCTC
Accession number: KCTC 13247BP
Accession date: 20170412

The invention claimed is:

1. A composition for blocking a *Vibrio parahaemolyticus* infection, inhibiting the development of diseases caused by a *Vibrio parahaemolyticus* infection, suppressing diseases caused by *Vibrio parahaemolyticus*, or alleviating the pathological condition of the diseases caused by *Vibrio parahaemolyticus*, comprising:

maltodextrin and $1 \times 10^4$ plaque-forming units per gram (pfu/g) to $1 \times 10^{15}$ pfu/g of proliferated and purified Myoviridae bacteriophage Vib-PAP-7, which has an ability to specifically kill *Vibrio parahaemolyticus* and a genome represented by SEQ ID NO: 1, and is deposited in the Korean Collection for Type Cultures (KCTC) under accession number KCTC 13247BP, wherein the maltodextrin and Myoviridae bacteriophage Vib-PAP-7 are in a dried mixture.

* * * * *